US012005194B2

(12) United States Patent
Galbraith et al.

(10) Patent No.: US 12,005,194 B2
(45) Date of Patent: *Jun. 11, 2024

(54) CONFIGURABLE OXYGEN CONCENTRATOR AND RELATED METHOD

(71) Applicants: Separation Design Group LLC, Waynesburg, PA (US); Belluscura LLC, Plano, TX (US)

(72) Inventors: Stephen Douglas Galbraith, Waynesburg, PA (US); Robert M. Rauker, Plano, TX (US)

(73) Assignees: SEPARATION DESIGN GROUP LLC, Waynesburg, PA (US); BELLUSCURA LLC, Plano, TX (US)

( * ) Notice: Subject to any disclaimer, the term of this patent is extended or adjusted under 35 U.S.C. 154(b) by 672 days.

This patent is subject to a terminal disclaimer.

(21) Appl. No.: 17/140,457

(22) Filed: Jan. 4, 2021

(65) Prior Publication Data

US 2021/0128865 A1    May 6, 2021

Related U.S. Application Data

(63) Continuation of application No. 16/482,427, filed as application No. PCT/US2018/035642 on Jun. 1, 2018, now Pat. No. 10,953,187.

(Continued)

(51) Int. Cl.
*A61M 16/10* (2006.01)
*A61M 16/00* (2006.01)

(52) U.S. Cl.
CPC ...... *A61M 16/101* (2014.02); *A61M 16/0063* (2014.02); *A61M 16/022* (2017.08);
(Continued)

(58) Field of Classification Search
CPC .............. A61M 16/101; A61M 16/022; A61M 16/0063; A61M 2205/3334;
(Continued)

(56) References Cited

U.S. PATENT DOCUMENTS

2006/0174874 A1   8/2006   Jagger et al.
2007/0137487 A1   6/2007   Whitley et al.
(Continued)

FOREIGN PATENT DOCUMENTS

CN    101522246 A    9/2009
JP    2005046632 A    2/2005
(Continued)

OTHER PUBLICATIONS

Office Action dated Jul. 5, 2022 in Chinese Application No. 201880037386.

(Continued)

*Primary Examiner* — Margaret M Luarca
(74) *Attorney, Agent, or Firm* — Panitch Schwarze Belisario & Nadel LLP

(57) ABSTRACT

A configurable oxygen concentrator for providing various flow rates and volumes of concentrated oxygen to a patient includes an electro-mechanical assembly having a housing with a first face, a second face and an outer surface. The oxygen concentrator also includes a first battery, a second battery, a first adsorbent container and a second adsorbent container. The first and second batteries are removably mountable to the first face and the first and second adsorbent containers are removably mountable to the second face to permit modification of the concentrated oxygen capacity and operating life of the concentrator as the patient progresses through different stages of a breathing disease. The first battery has a first battery capacity that is less than a second battery capacity of the second battery. The first adsorbent (Continued)

container has a first adsorbent capacity that is less than a second adsorbent capacity of the second adsorbent container.

21 Claims, 12 Drawing Sheets

Related U.S. Application Data

(60) Provisional application No. 62/660,533, filed on Apr. 20, 2018, provisional application No. 62/556,472, filed on Sep. 10, 2017, provisional application No. 62/515,859, filed on Jun. 6, 2017.

(52) U.S. Cl.
CPC . *A61M 2202/0208* (2013.01); *A61M 2205/18* (2013.01); *A61M 2205/3306* (2013.01); *A61M 2205/3317* (2013.01); *A61M 2205/3334* (2013.01); *A61M 2205/3379* (2013.01); *A61M 2205/502* (2013.01); *A61M 2205/6072* (2013.01); *A61M 2205/8206* (2013.01)

(58) Field of Classification Search
CPC .. A61M 2205/8206; A61M 2202/0208; A62B 7/08; B01D 53/047; B01D 2259/4533; B01D 2259/4541
See application file for complete search history.

(56) References Cited

U.S. PATENT DOCUMENTS

| | | |
|---|---|---|
| 2008/0087170 A1 | 4/2008 | Deane et al. |
| 2009/0018668 A1 | 1/2009 | Galbraith |
| 2009/0167698 A1 | 7/2009 | Altas et al. |
| 2009/0275896 A1* | 11/2009 | Kamen ............... A61M 5/172 |
| | | 604/151 |
| 2010/0043633 A1 | 2/2010 | Galbraith |
| 2012/0167886 A1 | 7/2012 | Taylor et al. |
| 2012/0192864 A1 | 8/2012 | Galbraith et al. |
| 2012/0266883 A1 | 10/2012 | Taylor et al. |
| 2015/0101603 A1 | 4/2015 | Galbraith et al. |
| 2015/0104524 A1 | 4/2015 | Galbraith et al. |

FOREIGN PATENT DOCUMENTS

| | | |
|---|---|---|
| TW | 200924809 A | 6/2009 |
| WO | 2009032540 A2 | 3/2009 |

OTHER PUBLICATIONS

Office Action dated Nov. 17, 2021 in Chinese Application No. 201880037386.

\* cited by examiner

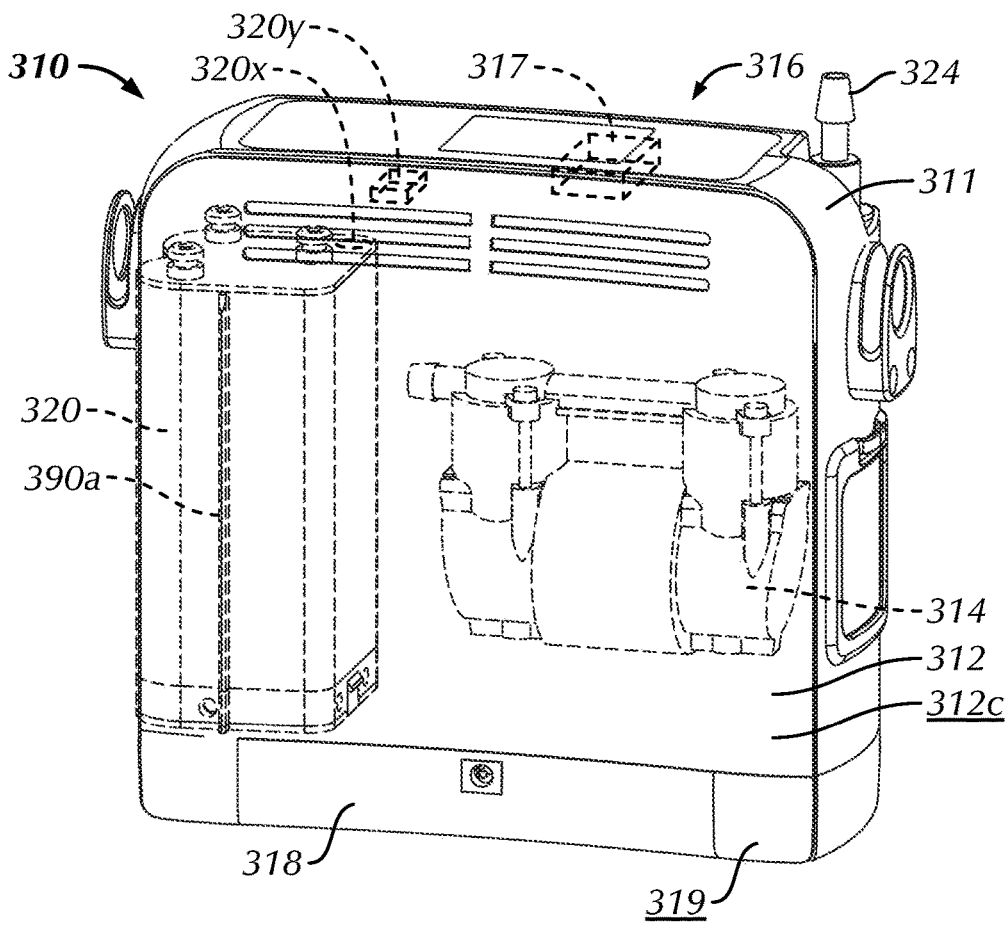
FIG. 12
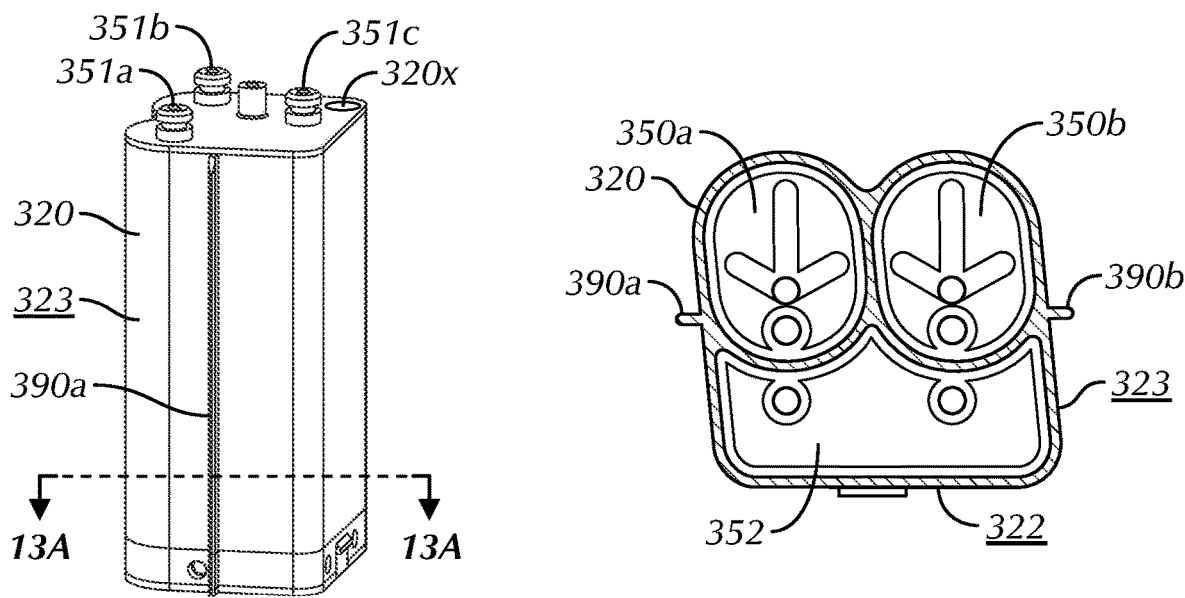
FIG. 13
FIG. 13A

CONFIGURABLE OXYGEN CONCENTRATOR AND RELATED METHOD

CROSS-REFERENCE TO RELATED APPLICATIONS

The present application is a continuation of U.S. patent application Ser. No. 16/482,427, filed Jul. 31, 2019 and titled, "Configurable Oxygen Concentrator and Related Method, which is U.S. National Phase Patent Application under Section 371 of International Patent Application No. PCT/US18/35642 filed Jun. 1, 2018 and titled "Configurable Oxygen Concentrator and Related Method," and claims the benefit of U.S. Provisional Patent Application Nos. 62/515,859, filed Jun. 6, 2017; 62/556,472, filed on Sep. 10, 2017 and 62/660,533, filed Apr. 20, 2018, each titled, "Configurable Oxygen Concentrator and Related Method," the disclosures of which are incorporated herein by reference in their entirety.

BACKGROUND OF THE INVENTION

Chronic Obstructive Pulmonary Disease (COPD) afflicts more that twelve (12) million people in the United States and many more throughout the world depending on local dietary, environmental, and personal lifestyle habits. COPD is a group of lung conditions that includes chronic bronchitis, emphysema, refractory asthma, and others. Restricted airflow, both in and out of a person's lungs, characterizes all these conditions. The inability to get enough oxygen into the lungs raises the risk for developing hypoxia. Preventing and reversing hypoxia involves increasing oxygen intake. A common method for providing extra oxygen is oxygen therapy. Oxygen therapy is also called supplemental or prescribed oxygen. Oxygen therapy typically consists of using a mechanical device that supplies oxygen to the patient's lungs, typically by nasal cannula. Traditionally oxygen has been carried in pressurized containers or as a liquid in a Dewar flask. More recently, electrically powered oxygen concentrators have been made available to patients.

These electronically powered concentrators produce an oxygen enriched gas flow by removing Nitrogen from air. The Nitrogen is removed from ambient air by a process called pressure swing adsorption ("PSA"). The resultant enriched gas flow can be as much as ninety-six percent (96%) pure Oxygen, the remainder substantially comprising inert Argon. The PSA process uses a material called zeolite, which has a greater affinity for Nitrogen than for Oxygen. Zeolites are typically comprised of microporous, aluminosilicate minerals including mostly silicone, aluminum, oxygen, and metals including titanium, tin, and zinc. Zeolite materials may be naturally occurring and synthetically produced. Containers of zeolite are first pressurized so the nitrogen can be adsorbed onto the zeolite crystal structure, and the resulting product flow becomes oxygen enriched. The container is then depressurized so the nitrogen can be exhausted to the atmosphere. This process is repeated in a cyclic manner to produced quantities of enriched oxygenated gas. Each cycle typically takes from one to seven seconds (1-7 sec). Usually two (2) containers of zeolite are used so there is a substantially constant flow of oxygen.

The PSA process for medical purposes may be used in stationary oxygen concentrators that weight up to fifty pounds (50 lbs) and produce as much as ten liters per minute ("LPM") of oxygen on a continuous or constant basis. These stationary oxygen concentrators are typically powered by electricity from an outlet. There are also portable PSA concentrators that typically weigh between two and eighteen pounds (2-18 lbs), producing smaller amounts of oxygen, and are battery powered, making them truly portable. One advantage of this type of concentrator is that it can be taken anywhere and recharged anywhere there is an electric outlet. Depending on the model, some have consumer removable batteries which can be swapped out easily when one battery loses power. Another advantage is that it is generally safer than pressurized or liquid delivery, which presents a fire or explosion risk. Portable oxygen concentrators, because of their low fire or explosion risk, are cleared by the US Federal Aviation Administration and the European Aviation Safety Agency for use on commercial aircraft. These types of portable concentrators are also used for high altitude workers, hikers, and skiers.

COPD is usually a progressive disease that can be measured by a forced expiratory volume ("FEV") test. The FEV test measures how much air a patient can exhale during a forced breath. The amount of exhaled air may be measured during a first second of the forced breath ("FEV1"), a second of the forced breath ("FEV2") and/or a third second of the forced breath ("FEV3"). The categories of severity of COPD typically range from stage 1: very mild with an FEV1 of approximately eighty percent (80%) to stage 4: very severe with an FEV1 of approximately thirty percent (30%) or lower and with low blood oxygen levels. Long term oxygen therapy ("LTOT") typically provides the greatest proven reduction in mortality among COPD patients and LTOT combined with walking is the generally considered the only therapy shown to significantly reduce mortality beyond a five (5) year threshold. In order to increase compliance with this therapy the oxygen source is preferably small and light enough to be carried by the patient without much effort.

The amount of oxygen that a concentrator can produce is roughly proportional to the amount of zeolite adsorbent that is contained in the PSA system. A very small concentrator may have only about eighty to one hundred grams (80-100 g) of adsorbent in the adsorbent module, which is typically sufficient to produce enough oxygen for a stage 1 patient. A larger portable PSA system may contain several hundred grams of adsorbent, but be suitable for a stage 2 or stage 3 patient. The size of the containers that hold the adsorbent also contribute to the size and weight of the concentrator and larger batteries are typically needed to support increased flow of oxygen in the higher capacity PSA systems. The PSA systems may include variably sized batteries to extend the working life while the user is detached from a direct electrical connection, with longer lasting batteries typically being larger and heavier, thereby being more difficult for the user to transport as the weight increases. Battery management and design including use of multiple battery sizes is described in U.S. Pat. No. 9,199,055 of Galbraith and titled, "Ultra Rapid Cycle Portable Oxygen Concentrator," the contents of which are incorporated herein by reference in their entirety. The adsorbent module of the PSA system may also be user replaceable, similar to the battery. Replacement of the adsorbent module is typically performed, as described in U.S. Pat. No. 8,894,751 of Galbraith and titled, "Ultra Rapid Cycle Portable Oxygen Concentrator," which is incorporated herein by reference in its entirety. The prior art adsorbent modules or beds are often rendered ineffective for nitrogen/oxygen separation due to moisture contamination and can be replaced by the patient without technical assistance instead of having to be sent to the factory or equipment supplier for repair.

It is desirable to provide a variety of sizes, weights, and flows of PSA concentrators so that patients can be best served at various stages of their disease. If a stage 1 patient is provided with a larger concentrator than needed, for example, a ten pound (10 lb) PSA system instead of a two and one-half pound (2½ lb) PSA system, the likelihood is that there will be reduced compliance to the recommended LTOT/walk therapy by the patient. PSA oxygen concentrator manufacturers and Durable Medical Equipment ("DME") providers typically make a range of concentrator sizes available to the patient's that meet the patient's requirements at each stage of the disease. This makes providing oxygen more expensive than it need be, as a patient is required to return and replace their PSA system as their disease progresses and the supplier is required to keep multiple sized PSA systems available for their multiple patients. In addition, manufacturing a range of concentrators is expensive for the manufacturer. Further, inventorying multiple concentrator types instead of just one adds both expense and complexity to the supply chain. Finally, the PSA concentrators must be exchanged (in case of leased equipment) or newly purchased if the patient buys the equipment as their disease progresses.

It would be desirable to design, construct and distribute a concentrator that has the flexibility to offer low flow and light-weight for the stage 1 patient, but can be upgraded for the stage 2 and stage 3 patients and, potentially, for the stage 4 patient, without having to exchange or discard the original concentrator. The preferred present invention addresses the shortcomings of the prior art devices and accomplishes certain of the above-described goals of maintaining the same or portions of the PSA system as the patient's disease progresses.

It would be further desirable to design, construct and offer a single portable oxygen concentrator that has a consumer/patient replaceable sieve module that can be internally dimensioned to operate at different levels. The preferred present invention addresses this shortcoming of the prior art.

It is still further desired to have a portable oxygen concentrator that has a consumer/patient replaceable sieve module that has the ability to receive or store medication, drugs or supplements in the oxygen reservoir to later be delivered to a patient via the concentrated oxygen stored in the reservoir which is later delivered to the patient.

BRIEF SUMMARY OF THE INVENTION

Briefly stated, a preferred embodiment of the present invention is directed to a portable and configurable oxygen concentrator for providing various flow rates and volumes of concentrated oxygen to a patient. The portable and configurable oxygen concentrator includes an electro-mechanical assembly having a housing with a first face, a second face and an outer surface. The oxygen concentrator also includes a first battery, a second battery, a first adsorbent container and a second adsorbent container. The first and second batteries are removably mountable to the first face and the first and second adsorbent containers are removably mountable to the second face of the electro-mechanical assembly to permit modification of the concentrated oxygen capacity and operating life of the concentrator as the patient progresses through different stages of a breathing disease. The first battery has a first battery capacity that is less than a second battery capacity of the second battery. The first adsorbent container has a first adsorbent capacity that is less than a second adsorbent capacity of the second adsorbent container.

In another aspect, the preferred system may be designed to have a single size, outer shell or outer dimensions and have the ability to operate at different levels with replaceable sieve modules or beds. The replaceable sieve modules or beds may include different types or sizes of zeolites contained in the module. The preferred modular system is able to operate at different levels to provide different concentrations of oxygen purity or concentrated oxygen with a single size sieve module or bed with differing internal materials or by operating the system in preferred sequences.

In yet another aspect, the preferred portable oxygen concentrator comprises a main housing with a battery releasably connected to the base of the portable concentrator housing. The housing encases, generally, a compressor, manifold, tubing, electronics and consumer replaceable adsorbent containers.

In another aspect, the preferred invention is directed to a portable and configurable oxygen concentrator for providing various flow rates and volumes of concentrated oxygen to a patient. The concentrator includes an electro-mechanical assembly having a housing with an outer surface, a first battery, a first adsorbent container, a second adsorbent container and a controller. The housing encloses a compressor. A user interface is mounted to the housing. The first battery has a first battery capacity and is removably mountable to the electro-mechanical assembly to form a substantially continuous surface between the first battery and the outer surface in a working configuration. The first adsorbent container has a first adsorbent capacity. A first notification device is associated with the first adsorbent container. The second adsorbent container has a second adsorbent capacity. A second notification device is associated with the second adsorbent container. The controller is in communication with the first notification device or the second notification device in the working configuration. The controller is configured to operate to produce a first oxygen volume of purified oxygen when the first adsorbent container is mounted to the electro-mechanical assembly and to produce a second oxygen volume of purified oxygen when the second adsorbent container is mounted to the electro-mechanical assembly. The second oxygen volume is greater than the first oxygen volume.

BRIEF DESCRIPTION OF THE SEVERAL VIEWS OF THE DRAWINGS

The foregoing summary, as well as the following detailed description of preferred embodiments of the configurable oxygen concentrator, assembly and method of the preferred present invention, will be better understood when read in conjunction with the appended drawings. For the purposes of illustrating the configurable oxygen concentrator, there is shown in the drawings preferred embodiments. It should be understood, however, that the preferred present invention is not limited to the precise arrangements and instrumentalities shown. In the drawings:

FIG. 12 is a rear perspective view of the configurable oxygen concentrator of FIG. 7, wherein an adsorbent container and compressor are shown within a housing of the configurable oxygen concentrator;

FIG. 13 is a side perspective view of an adsorbent container of the configurable oxygen concentrator of FIG. 7;

FIG. 13A is a cross-sectional view of the adsorbent container of FIG. 13, taken along line 13A-13A of FIG. 13;

DETAILED DESCRIPTION OF THE INVENTION

Figure 1:
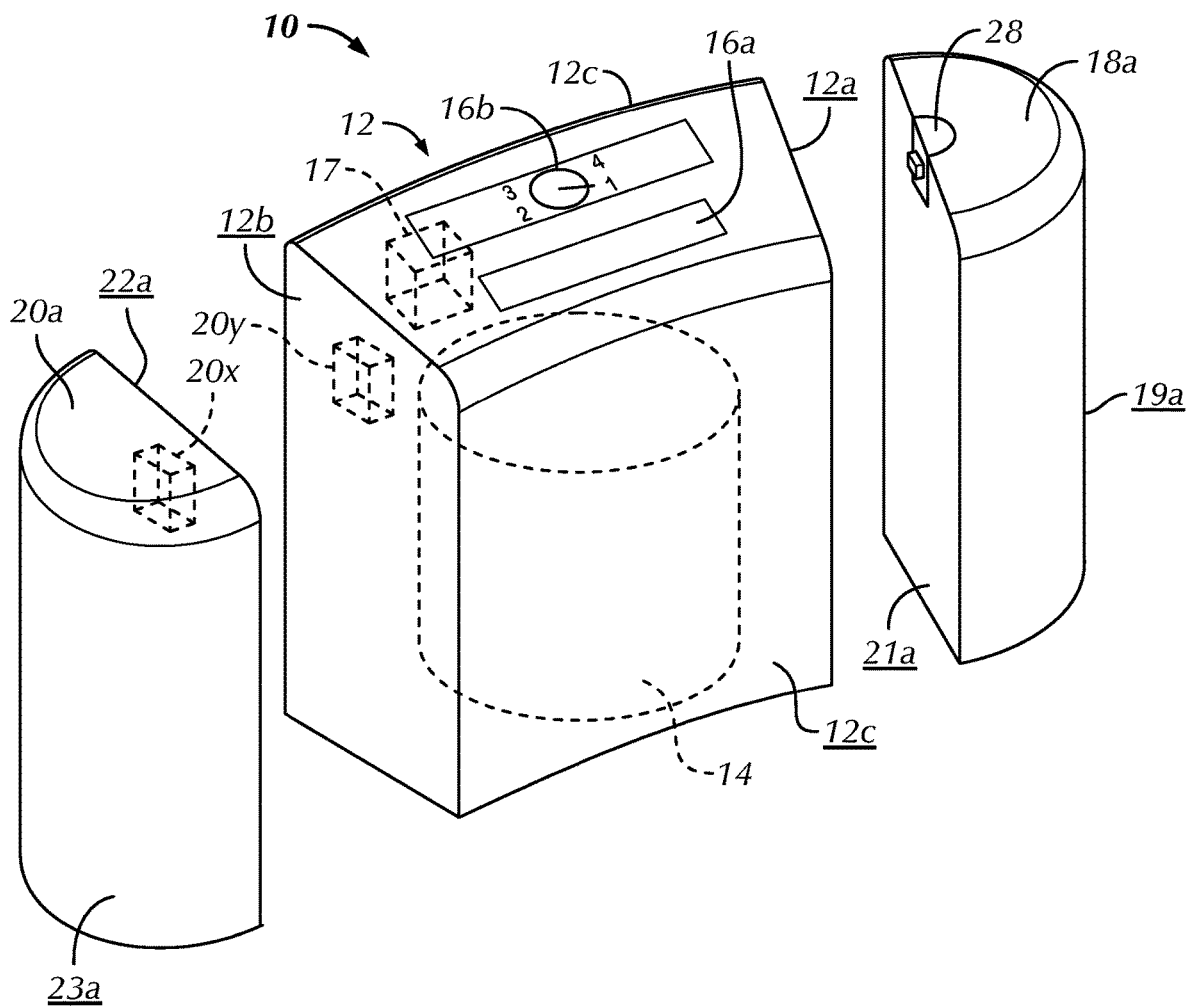
FIG. 1 is a front perspective, partially exploded view of a portable and configurable oxygen concentrator in accordance with a first preferred embodiment of the present invention.

Certain terminology is used in the following description for convenience only and is not limiting. Unless specifically set forth herein, the terms "a", "an" and "the" are not limited to one element but instead should be read as meaning "at least one". The words "right", "left", "lower" and "upper" designate directions in the drawings to which reference is made. The words "inwardly" or "distally" and "outwardly" or "proximally" refer to directions toward and away from, respectively, the patient's body, or the geometric center of the preferred configurable oxygen concentrator and related parts thereof. The words, "anterior", "posterior", "superior," "inferior", "lateral" and related words and/or phrases designate preferred positions, directions and/or orientations in the human body or the preferred oxygen concentrator to which reference is made and are not meant to be limiting. The terminology includes the above-listed words, derivatives thereof and words of similar import.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Figure 2:
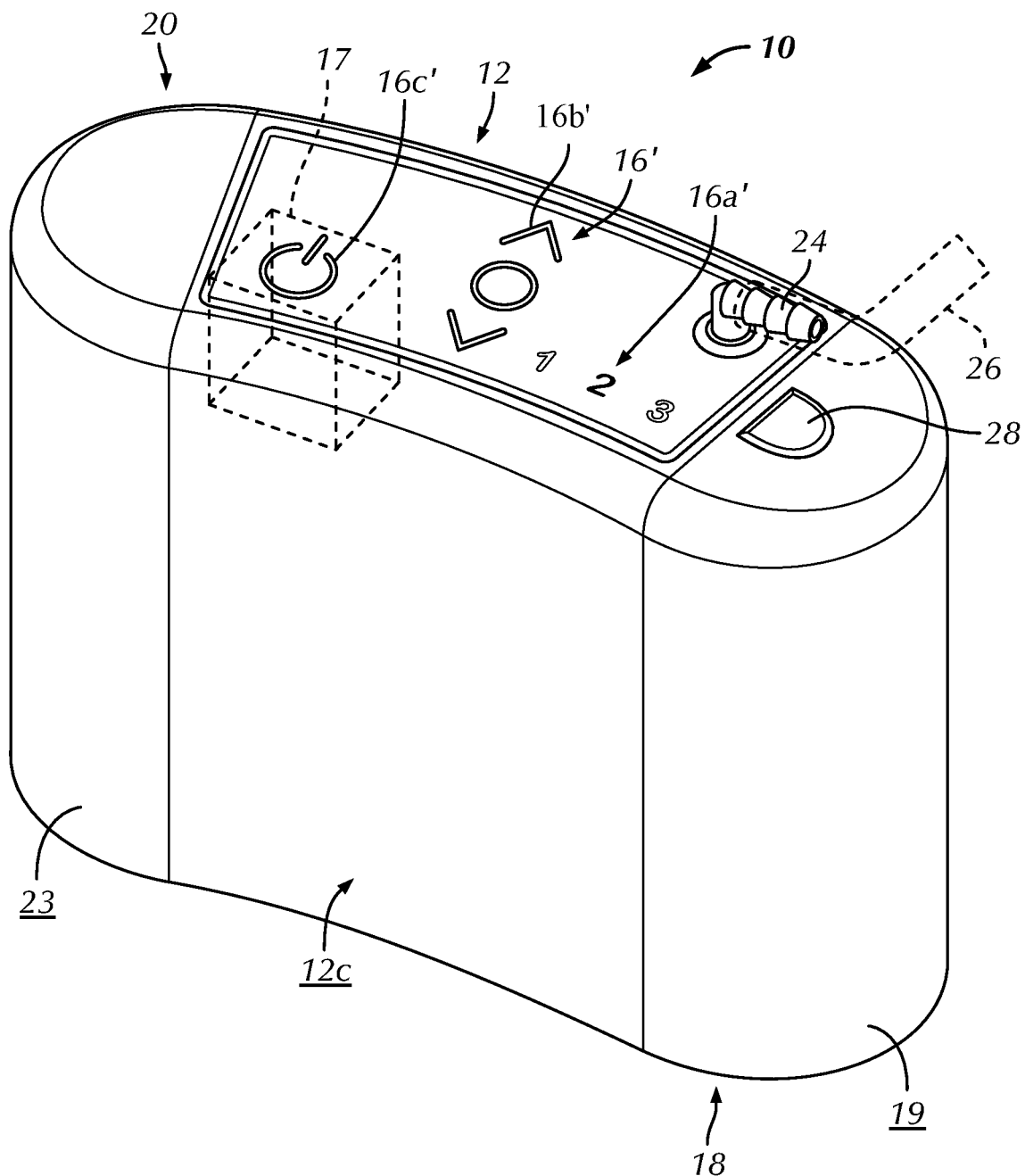
FIG. 2 is a front perspective view of the configurable oxygen concentrator of FIG. 1, with an alternative user interface on a top surface.

Referring to FIGS. 1 and 2, a portable and configurable oxygen concentrator, generally designated 10, in accordance with a first preferred embodiment is typically designed having three components. The main component is a concentrator electro-mechanical assembly 12. The electro-mechanical assembly 12 typically includes a compressor 14, various electronics components, valves, a conserver, a user interface 16, a purity monitor, a case, and ancillary hoses and connectors. The user interface 16 preferably includes a display 16a, a selector dial 16b and a power button 16c. The electro-mechanical assembly 12 has a first face 12a and a second face 12b that are configured to accommodate attachable components. The attachable components preferably include batteries 18 and adsorbent containers 20. The selector dial 16b may be comprised of a dial or switch that is turned or actuated, manually or by voice, to select operating levels, an up and down control button that permits increase or decrease of the operating level of the configurable oxygen concentrator 10, a visual representation of the selector dial or control button 16b on the display 16a, which may be comprised of a touchscreen or other mechanisms or systems that are able to permit user selection of operating levels of the configurable oxygen concentrator 10. The power button 16c is preferably comprised of a button that turns the power off and on for the configurable oxygen concentrator 10 and may, likewise, be comprised of a button representation of a touchscreen or another mechanism or system for actuating power.

Referring to FIG. 2, the first preferred portable oxygen concentrator 10 may include an alternative preferred user interface 16' that has similar features when compared to the first preferred user interface 16 and the same reference numbers are utilized to identify the similar features with a prime symbol (') used to distinguish the features of the alternative preferred user interface 16' from the first preferred user interface 16. The alternative preferred user interface 16' includes the display 16a', a selector 16b' that functions as the selector dial 16b and the power button 16c'. The display 16a' shows three operating settings for the configurable oxygen concentrator 10, identified by the numbers "1," "2," and "3," which may represent the concentrator 10 working at three different operating levels, oxygen delivery volumetric flow rates or oxygen volumes, such as flow rates of two hundred milliliters per minute (200 ml/min) at level "1," four hundred milliliters per minute (400 ml/min) at level "2" and six hundred milliliters per minute (600 ml/min) of concentrated oxygen at level "3." The flow rates, volumes and levels are not limiting, but are provided as non-limiting examples for the preferred portable oxygen concentrator 10. The operating levels are preferable modified by manipulating the selector 16b' to move the levels up and down, based on physician prescription, user preferences or other factors.

Figure 3:
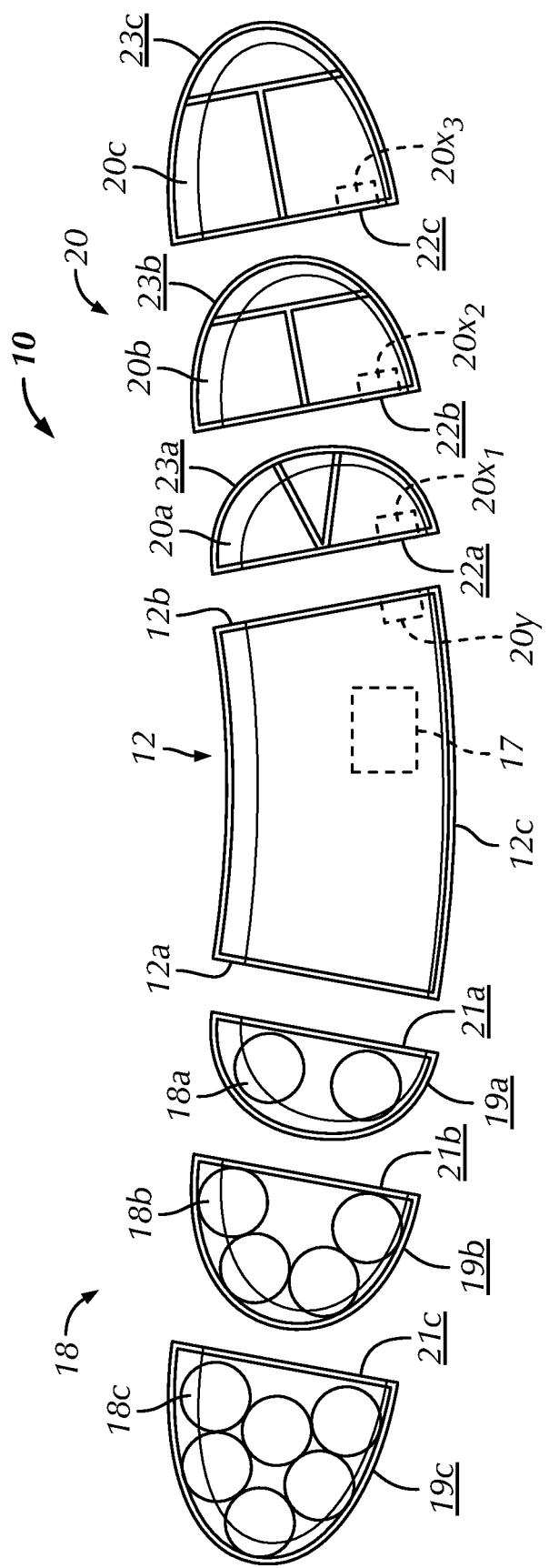
FIG. 3 is a top plan, partially exploded view of the configurable oxygen concentrator of FIG. 1, including additional batteries and adsorbent containers utilized with the configurable oxygen concentrator.

Referring to FIGS. 1-3, the electro-mechanical assembly 12 of the first preferred embodiment also includes an oxygen output fitting 24 that is removably connectable to an oxygen hose 26 that directs the concentrated oxygen to the patient's nose and airway. The oxygen output fitting 24 preferably extends out of the top surface of the electro-mechanical assembly 12 near the user interface 16, 16' for user convenience, but is not so limited, and may extend out of nearly any portion of the electro-mechanical assembly 12, as long as the oxygen output fitting 24 is in fluid communication with concentrated oxygen produced by the configurable oxygen concentrator 10. The oxygen output fitting 24 is preferably pivotable relative to the electro-mechanical assembly 12 so that the user may adjust the positioning of the oxygen output fitting 24 for convenience.

In the first preferred embodiment, the batteries 18 may be of various sizes, weights, quantiles and energy content. The batteries 18 of the first preferred embodiment include a relatively small or first battery 18a having a first battery capacity that is removably attachable to the first face 12a for operation of the electro-mechanical assembly 12 for a stage one (1) patient who generally requires a relatively low flow rate of concentrated oxygen during use. At this relatively low flow rate the compressor 14 uses relatively little energy and the small battery 18a powers the portable and configurable oxygen concentrator 10 long enough for the patient to have a reasonable range of operation, such as walking a few miles or going to the store. The small or first battery 18a is preferably at least electrically secured to the electro-mechanical assembly 12 at the first face 12a and is preferably secured, fastened or bonded to the first face 12a to join the small battery 18a to the electro-mechanical assembly 12 in a working configuration. The first battery 18a is preferably secured to the first face 12a by fasteners, magnetic mechanisms, adhesive bonding, hook and loop material, a tongue and groove fastening mechanism, strapping or other securing mechanisms that secure or join the first battery 18a to the first face 12a in the working configuration. The first battery 18a is preferably secured to the electro-mechanical assembly 12 to form a substantially consistent and continuous outer surface in the working configuration. That is, in the working configuration, the outer surface 19a of the first battery 18a defines or forms a substantially continuous outer surface with an outer surface 12c of the electro-mechanical assembly 12, specifically proximate edges of the first face 12a. In the working configuration, accordingly, a joining face 21a of the first battery 18a is positioned proximate and substantially overlaps the first face 12a of the electro-mechanical assembly 12. The second and third battery 18b, 18c also preferably include outer surfaces 19b, 19c, respectively, and the outer surfaces 19 of the batteries 18a, 18b, 18c are preferably identified generically by the reference number "18."

If longer or higher volume operation is desired, the next larger, mid-sized or second battery 18b having a second capacity that is greater than the first capacity of the first battery 18a is preferably removably attached to the first face 12a. The second battery 18b preferably attaches to the first face 12a of the electro-mechanical assembly 12 in the same or substantially the same manner as the small or first battery 18a, such that a joining face 21b of the second battery 18b substantially overlaps the first face 12a. If still further longer or higher volume operation is desired, the next larger, large or third battery 18c having the third capacity which is greater than the second capacity of the second battery 18b is preferably removably attached to the first face 12a. The third battery 18c preferably attaches to the first face 12a of the electro-mechanical assembly 12 in the same or substantially the same manner as the first and second batteries 18a, 18b, such that a joining face 21c of the third battery 18c substantially overlaps the first face 12a. The preferred configurable oxygen concentrator 10 is not limited to including the first, second and third batteries 18a, 18b, 18c and may include more or less batteries 18a, 18b, 18c that are sized and configured for operating the electro-mechanical assembly 12 for various amounts of time and at various volumes of concentrated oxygen flow. The preferred configurable oxygen concentrator 10 may include nearly any number of batteries 18a, 18b, 18c that are desired by a user or designer that are able to perform the preferred functions of the configurable oxygen concentrator 10 and withstand the normal operating conditions of the configurable oxygen concentrator 10, as is described herein. The management of battery weight in concentrators is often accomplished by varying the number or size of the batteries 18a, 18b, 18c to provide the patient with flexibility in use. For example, the first or small and relatively light-weight battery 18a may be used for short trips and the relatively heavier second/mid-sized or larger or third batteries 18b, 18b may be used for long trips that are facilitated by longer use of the configurable oxygen concentrator 10.

The batteries 18 also preferably include a release button 28 on a top surface that releases the batteries 18 from the electro-mechanical assembly 12 and assists in locking the batteries 18 to the electro-mechanical assembly 12 during use. The release button 28 is not limited to being positioned on the top surface and may be positioned in nearly any location of the batteries 18 to releasably engage the electro-mechanical assembly 12.

The first preferred configurable oxygen concentrator 10 also includes user selectable adsorbent containers 22 that are removably mountable to the second face 12b of the electro-mechanical assembly 12. The adsorbent containers 22 have maximum capacities that limit the amount or volume of concentrated oxygen that can be produced during a single cycle when used with the electro-mechanical assembly 12. It is generally not necessary for a stage one (1) patient to carry around extra adsorbent material if it is not needed to concentrate the predetermined volume of oxygen that the patient requires for therapy. The patient will probably rent or purchase a small concentrator that is limited to the flow rate that is prescribed. The adsorbent containers 22 typically become larger and heavier as the volume of concentrated oxygen increases. Alternatively, the adsorbent containers 22 can remain the same size, but certain containers are able to process more concentrated oxygen by making the adsorbent contain adsorbent beads of a smaller diameter or other different physical/chemical make-up that allows for larger oxygen flow rate. These adsorbent containers or beds 22 can be heavier or more expensive and are preferably used when the physician prescribes the higher flow rate. The design of the preferred configurable oxygen concentrator 10 provides the electro-mechanical assembly 12 with components that are common to a wide variety of flow values with the capability of attaching to the multiple adsorbent containers 20. The electronics and valving of the electro-mechanical assembly 12 are generally independent of the concentrator size and the compressor 14 is preferably chosen to be capable of providing enough air flow for the contemplated range of product oxygen flow rates, such that the compressor 14 is large enough to produce the maximum amount of concentrated oxygen volume of the largest of the adsorbent containers 20. Thus, a stage one (1) patient would be provided with a preferred concentrator 10 with a relatively small light-weight or first adsorbent module or container 20a attached to the electro-mechanical assembly 12.

In the first preferred embodiment, the adsorbent containers 20 include the first adsorbent container 20a, a second or medium adsorbent container 20b and a third or large adsorbent container 20c. The configurable oxygen concentrator 10 is not limited to including the three preferred adsorbent containers 20a, 20b, 20c and may include more or less adsorbent containers 20, based on patient needs and/or designer preferences. The configuration of the patient replaceable adsorbent modules or containers 20 is extended in this invention, in comparison to prior art devices, to allow the patient, on directions from her/his physician, to increase the capacity of their configurable oxygen concentrator system 10 simply by exchanging, for example, the smaller or first adsorbent module or container 20a for a second/medium or third/large adsorbent container 20b, 20c. The first preferred adsorbent container 20a preferably has a first adsorbent capacity that is less than a second adsorbent capacity of the second adsorbent container 20b and the third preferred adsorbent container 20c preferably has a third adsorbent capacity that is greater than the second adsorbent capacity of the second adsorbent container 20b. When the adsorbent container 20 is installed by the patient the adsorbent container 20 is automatically identified by the electro-mechanical assembly 12 so that the electro-mechanical assembly 12 operates in accordance with the particular adsorbent container 20a, 20b, 20c attached to the electro-mechanical assembly 12 in the working configuration. The electro-mechanical assembly 12 may, specifically, operate in different flow settings, timing, pressure ranges, compressor loads, compressor speeds, valve sequences, etc. based on the specific adsorbent container 20a, 20b, 20c that is mounted to the electro-mechanical assembly 12.

The first adsorbent container 20a preferably has the first adsorbent capacity that may be based on a volume of adsorbent material, the type of adsorbent material, the size of orifices communicating with a vessel containing the adsorbent material or other related features that impact the adsorbent capacity of the first adsorbent container 20a. The second adsorbent container 20b preferably has the second adsorbent capacity that is greater than the first adsorbent capacity and the third adsorbent capacity 20c preferably has the third adsorbent capacity that is greater than the first and second adsorbent capacities. The capacities of the first, second and third capacities of the first, second and third adsorbent containers 20a, 20b, 20c may be adjusted by including a first volume of adsorbent material in the first adsorbent container 20a, a second volume of adsorbent material in the second adsorbent container 20b and a third volume of adsorbent material in the third adsorbent container 20c, wherein the third volume is greater than the second volume and the second volume is greater than the first volume. Alternatively, the first adsorbent container 20a may include a first adsorbent material therein and the second adsorbent container 20b may include a second adsorbent material therein, wherein the first adsorbent material is different than the second adsorbent material and the second adsorbent material provides a greater adsorbent capacity than the first adsorbent material. The first and second adsorbent materials are preferably comprised of a zeolite material.

The first adsorbent container 20a preferably includes a first notification device $20x_1$ associated therewith or mounted thereto. The second adsorbent container 20b also preferably includes a second notification device $20x_2$ and the third adsorbent container 20c includes a third notification device $20x_3$. Generically, the first, second and third notification devices $20x_1, 20x_2, 20x_3$ may be referred to herein as the notification device 20x, which is utilized to indicate the capacity of the particular adsorbent container 20, such as the first, second and third adsorbent containers 20a, 20b, 20c. In the first preferred embodiment, the first, second and third notification devices $20x_1, 20x_2, 20x_3$ are comprised of first, second and third magnets, respectively. The first, second and third notification devices $20x_1, 20x_2, 20x_3$ are not limited to being comprised of magnets and may be comprised of any element or feature that may be utilized to identify the capacity of the specific adsorbent container 20, such as a bar code, a mechanical assembly, a mechanical feature, a visual feature, a visual feature or nearly any feature that may be utilized to specifically identify the particular adsorbent container 20 and the capacity of the adsorbent container 20. The notification devices 20x are preferably mountable to the adsorbent containers 20 for communication with the electro-mechanical assembly 12 to identify the capacity of the specific adsorbent container 20 and the related capacity.

In the first preferred embodiment, a controller 17 is mounted in the electro-mechanical assembly 12 and is in communication with the first, second or third notification devices $20x_1, 20x_2, 20x_3$ in the working configuration and, particularly, is in communication with the notification device 20x of the adsorbent container 20a, 20b, 20c that is mounted to the electro-mechanical assembly 12. The communication between the electro-mechanical assembly 12, related sensors and the adsorbent containers 20 may be via electrical connections, magnetic sensors, physical switches, wireless communication, mechanical assemblies, optical switches or other sensors or transmitters.

In the first preferred embodiment, a notification sensor 20y is mounted to the electro-mechanical assembly 12, preferably proximate the second face 12b or the face 12b where the adsorbent container 20 is mounted to the electro-mechanical assembly. The notification sensor 20y is not limited to being mounted proximate the second face 12b, but is preferably so mounted for communication with the notification device 20x. The notification sensor 20y is preferably in communication with the controller 17 and transmits a signal to the controller 17 in the working configuration regarding which of the adsorbent containers 20 is mounted to the electro-mechanical assembly 12. In the first preferred embodiment, the notification sensor 20y is a Hall effect sensor that senses the presence of the notification devices 20x, which are preferably comprised of magnets. The notification sensor 20y is not limited to being comprised of the Hall effect sensor and may be comprised of nearly any sensor that is able to detect the various notification devices 20x, communicate the sensed notification device 20x to the controller 17 and withstand the normal operating conditions of the notification sensor 20y. For example the notification sensor 20y may be comprised of a visual or optical sensor that detects a bar code or other visual indication on the adsorbent containers 20, a mechanical assembly that detects different mechanical features of the adsorbent containers 20 or other sensors that are able to detect the difference between the adsorbent containers 20 in the working configuration. When the notification sensor 20*y* is a visual or optical sensor, the first adsorbent container 20*a* may include a first barcode 20$x_1$, the second adsorbent container 20*b* may include a second barcode 20$x_2$ and the third adsorbent container 20*c* may include a third barcode 20$x_3$ that are optically detected by the notification sensor 20*y* for transmittal to the controller 17 and appropriate operation of the configurable oxygen concentrator 10. The notification sensor 20 may also be comprised of a proximity sensor that senses the proximity of the notification device 20*x* mounted to the adsorbent container 20, which may correspond to the particular adsorbent container 20 mounted to the electro-mechanical assembly 12 in the working configuration. The notification sensor 20*y* preferably detects that particular notification device 20*x* of the various adsorbent containers 20 and provides a signal to the controller 17 so that the controller 17 operates the configurable oxygen concentrator 10 based on identification of the specific adsorbent container 20.

In operation, for example, when the notification sensor 20*y* sends a signal to the controller 17 indicating the first adsorbent container 20*a* is mounted to the electro-mechanical assembly 12 in the working configuration, the controller 17 may change the timing of valves associated with air and oxygen flow to and from the first adsorbent container 20*a*. The controller 17 may alternatively or in combination limit the flow settings available to the user and, thereby, operate the compressor 14 at a first speed that is lower than second or third speed when the second and third adsorbent containers 20*b*, 20*c* are attached to the electro-mechanical assembly 12. In contrast, when the notification sensor 20*y* sends a signal to the controller 17 indicating the second adsorbent container 20*b* is mounted to the electro-mechanical assembly 12 in the working configuration, the controller 17 may change the timing of the valves associated with air and oxygen flow to and from the second adsorbent container 20*b* to provide additional purified oxygen capacity to the user. The controller 17 may alternatively or in addition, increase or decrease a pressure swing adsorption ("PSA") valve timing duration and may allow the user access to additional or higher flow settings when the second adsorbent container 20*b* is identified as attached to the electro-mechanical assembly 12. Further, the controller 17 may also change the timing of the valves associated with the air and oxygen flow to and from the third adsorbent container 20*c* when the notification sensor 20*y* sends a signal to the controller 17 indicating the third adsorbent container 20*c* is mounted to the electro-mechanical assembly 12 in the working configuration. The controller 17 may further expand the flow settings available to the user when the third adsorbent container 20*c* is identified as being mounted to the electro-mechanical assembly in the working configuration. As a non-limiting example, when the controller 17 receives a signal that the first adsorbent container 20*a* is attached to the electro-mechanical assembly 12, three (3) settings may be indicated as available on the selector dial 16*b*, such as "1," "2," and "3" that result in the concentrator 100 providing two hundred milliliters per minute (200 ml/min), four hundred milliliters per minute (400 ml/min) and six hundred milliliters per minute (600 ml/min) of purified oxygen, respectively, to the patient. This range of approximately two hundred milliliters per minute to six hundred milliliters per minute (200-600 ml/min) represents a first oxygen volumetric flow rate range or first oxygen volume. The controller 17 may alternatively indicate or make available five (5) settings on the selector dial 16*b*, such as "1," "2," "3," "4," and "5" when the second adsorbent container 20*b* is attached to the electro-mechanical assembly 12 that result in the concentrator 100 providing two hundred milliliters per minute (200 ml/min), four hundred milliliters per minute (400 ml/min), six hundred milliliters per minute (600 ml/min), eight hundred milliliters per minute (800 ml/min) and one thousand milliliters per minute (1,000 ml/min) of purified oxygen, respectively, to the patient. This range of approximately two hundred milliliters per minute (200 ml/min) to one thousand milliliters per minute (200-1000 ml/min) represents a second oxygen volumetric flow rate range or second oxygen volume. Although the first oxygen volume and the second oxygen volume overlap, the second oxygen volume when the second adsorbent container 20*b* is attached is greater than the first oxygen volume when the first adsorbent container 20*a* is attached, thereby providing a potential greater volumetric purified oxygen flow for the patient when the second adsorbent container 20*b* is attached to the electro-mechanical assembly 12. Likewise, attaching the third adsorbent container 20*c* to the electro-mechanical assembly 12 preferably facilitates a third oxygen volume or third volumetric flow rate that may overlap, but includes an upper limit greater than the second oxygen volume.

Any data acquired by the electro-mechanical assembly related, but not limited to location of the concentrator 10, global positioning system ("GPS") tracking, movement, battery power, usage time, oxygen purity, performance, presence of the batteries 18, presence of the adsorbent containers 20, patient breathing rate, oxygen flow, concentrated oxygen pressure, timer, usage rate, environmental factors such as temperature, humidity, and related factors, power draw rate and related acquired data may be collected and stored in the controller 17 in the electro-mechanical assembly 12. The controller 17 may be in wired or wireless communication with a central processor (not shown) that may be access by the patient's physician or other personnel. The collected data may be utilized by the physician or other personnel for diagnosis, treatment, reimbursement, monitoring or other purposes to track the usage and effectiveness of treatment for the patient. The controller 17 may be in communication with the central processor by Wi-Fi, Bluetooth, or other wireless communication protocol and may be available for review on a mobile software application by the patient, physician or other personnel so that the data may be tracked. The data may include location of the concentrator 10, battery power, oxygen purity, GPS tracking, performance, and related information. In addition, the mobile application may provide warnings to the patient, physician or other personnel if the patient does not use the concentrator during a predetermined amount of time, oxygen purity falls below a predetermined level, battery power is below a predetermined level or for other reasons that may be determined based on the data collected during use. The preferred modular oxygen concentrator 10 is able to produce two hundred milliliters per minute (200 ml/min), four hundred milliliters per minute (400 ml/min) and six hundred milliliters per minute (600 ml/min) when the first adsorbent container 20*a* is mounted to the electro-mechanical assembly 12. When the second adsorbent container 20*b* is mounted to the electro-mechanical assembly 12, the concentrator 10 is preferably also able to produce eight hundred milliliters per minute (800 ml/min) of purified oxygen or more. When the third adsorbent container 20*c* is mounted to the electro-mechanical assembly 12, the concentrator 10 is able to produce one thousand milliliters per minute (1000 ml/min) of purified oxygen, or more. The modular oxygen concentrator 10 may alternatively be able to produce different levels or have different capacities, but is not so limited and may be otherwise designed and configured to produce alternative equivalent volumes of concentrated oxygen and different purities of oxygen, as desired by the designer or required by the patient.

The first preferred adsorbent modules or containers 20a, 20b, 20c, similar to the batteries 18, include joining faces 22a, 22b, 22b, respectively that substantially overlap the second face 12b of the electro-mechanical assembly 12 in the working configuration. In addition, the adsorbent modules or containers 20a, 20b, 20c, similar to the batteries 18, include outer surfaces 23a, 23b, 23c, respectively that form a substantially continuous outer surface with the outer surface 12c of the electro-mechanical assembly 12c in the working configuration, specifically proximate edges of the second face 12b. In the working configuration, accordingly, the joining faces 22a, 22b, 22c of the adsorbent modules or containers 20a, 20b, 20c are positioned proximate and substantially overlap the second face 12b of the electro-mechanical assembly 12 and the outer surfaces 23a, 23b, 23c of the adsorbent modules 20a, 20b, 20c form a substantially continuous surface with the outer surface 12c of the electro-mechanical assembly 12 such that significant discontinuities between the outer surfaces 12a, 23b, 23c, 12c are not present and the configurable oxygen concentrator 10 has a single unit appearance in the working configuration. The configurable oxygen concentrator 10 is not limited to such single unit appearance and may be constructed such that the batteries 18 are generally separate and only electrically connected to the electro-mechanical assembly 12 and the adsorbent modules 20 are connected by extendable tubes or hoses to the electro-mechanical assembly 12.

In the first preferred embodiment, removing and replacing the adsorbent modules 20 is as easy as removing and replacing the batteries 18 to the electro-mechanical assembly 12. The adsorbent modules 20 are preferably connected to the electro-mechanical assembly 12 such that all pneumatic connections are made by aligning the individual adsorbent module 20a, 20b, 20c with the electro-mechanical assembly 12 and then securing by some sort of physical securing mechanism, similar to the mechanisms and methods described above for the batteries 18. Thus, when the physician sees that the patient had moved from an early stage of a breathing disease, such as COPD, to a later more severe stage and prescribes a larger flow of oxygen, the patient has only to order the larger flow rate adsorbent modules 22b, 22c at a small fraction of the price of a new larger oxygen concentrator. In addition, the patient may be provided with multiple sizes of adsorbent modules 22a, 22b, 22c when first issued the configurable oxygen concentrator 10 and the patient may then remove and replace the appropriate adsorbent modules 22a, 22b, 22c to transition from a lower volume concentrator to a higher volume concentrator. Instead of going through several concentrators, as is typically the case with prior art oxygen concentrators, the patient uses the preferred configurable oxygen concentrator 10 for the duration of the therapy and merely upgrades, as required, by customizing the adsorbent module 22a, 22b, 22c that is attached to the electro-mechanical assembly 12, as is described herein. Thus the cost of changing to a higher capacity oxygen concentrator is dramatically reduced when compared to the prior art oxygen concentrators that had to be completely returned and replaced when moving to a different capacity unit. In addition, the weight, size and cost of the configurable oxygen concentrator 10 is substantially matched to the patient's requirements, such as by pairing the small battery 18a with the small adsorbent module 22a when the patient is in early stages of the breathing disease and is relatively mobile so that a relatively light oxygen concentrator 10 is preferred and pairing the relatively high capacity, but heavier oxygen concentrator 10 with the large battery 18c and the large flow rate adsorbent module 20c when the patient is in later stages of the breathing disease. In the first preferred embodiment, the patient retains the ability to adjust the configurable oxygen concentrator 10 for long or short duration activities by proper selection of battery sizes, including selection of the progressively sized batteries 18a, 18b, 18c of the first preferred embodiment.

Progressive respiratory and breathing diseases, such as chronic obstructive pulmonary disease ("COPD"), generally result in therapies requiring increasing levels and amounts of oxygen or purified oxygen supplied to the patient. This increasing supply of oxygen or purified oxygen is typically accomplished by supplying the patient with progressively larger and increasingly expensive oxygen concentrators having increased flow and concentration capacity. These prior art devices typically require return or disposal of the original device and purchase of a new higher capacity concentrator as the patient's disease progresses or becomes more severe. The modularity of the preferred portable oxygen concentrator 10 prevents the need to return or dispose of a lower capacity oxygen concentrator as the patient's disease progresses.

The first preferred portable and modular oxygen concentrator 10 has three basic subassemblies, including the electro-mechanical assembly or core 12, the series of batteries 18a, 18b, 18c and the series of sieve modules or adsorbent containers 20a, 20b, 20c. The electro-mechanical assembly preferably includes the electronics or control mechanisms, valves, and the compressor 14 that have the capacity to produce the largest anticipated flow rate that will be required for the patient during the course of the disease. The batteries 18 preferably include first, second and third different sized batteries 18a, 18b, 18c that can operate the concentrator 10 for relatively short, medium, and long durations, depending on the size of the battery 18a, 18b, 18c selected and the electric draw of the concentrator 10. The series of adsorbent containers or sieve beds 20 is replaceable in case they becomes non-functional and so that the adsorbent containers 20 can be interchanged to increase or decrease the capacity to separate oxygen from air or the volume of concentrated oxygen produced. The adsorbent containers 20a, 20b, 20c may become non-functional for various reasons, including normal wear and tear, exposure of the internal sieve material to moisture or other performance degradation factors. The patient is preferably able to remove and replace the sieve modules or adsorbent containers 20a, 20b, 20c to and from the electro-mechanical assembly 10 without technical assistance.

In use, a physician prescribes a higher flow rate of oxygen for the patient as their disease progresses, the patient or the concentrator supplier can provide increasingly larger adsorbent containers 20a, 20b, 20c that permit the concentrator 10 to attain the increases flow rate without exchanging the electro-mechanical assembly 12. The sieve module or adsorbent containers 20 typically cost only a fraction of the price of the electro-mechanical assembly 12 and both the patient and the provider save money when utilizing the modularity of the preferred concentrator 10. The concentrator 10 can be configured to produce the needed flow rate while having the least mass or weight to improve portability for the patient.

Referring to FIGS. 1-4, the adsorbent containers 20 include a locking mechanism 30 to secure the adsorbent containers 20 to the second face 12b of the electro-mechanical assembly 12 in a mounted configuration. The locking mechanism 30 is preferably comprised of a clasp or tang 30a, a translatable rod 30b and a locking hole 30 in the second face 12b of the electro-mechanical assembly 12. The translatable rod 30b is movably secured completely within the housing of the adsorbent containers 20 adjacent the second face 12b such that the rod 30b is movable generally parallel to the second face 12b. In the first preferred embodiment, the translatable rod 30b is secured inside the adsorbent containers 20 to an upper shelf 32a and a lower shelf 32b that both include holes therethrough through which the upper and lower portions of the translatable rod 30b are movable. The translatable rod 30b and the clasp 30a are biased toward the lower shelf 32b by a biasing member or compression spring 34. The clasp 30a includes a ramped surface 30d spaced from the proximal end of the clasp 30a which is attached to the translatable rod 30b. The adsorbent containers 20 also include a release hole 36 that is substantially aligned with the translatable rod 30b proximate the joining face 22. The translatable rod 30b may be selectively moved by the user by inserting a release tool 31 through the release hole 36 and pushing the translatable rod 30b toward the upper shelf 32a against the bias of the spring 34.

The adsorbent containers 20 also include a bumper 38 extending from the joining face 22 and an airflow fitting 40. The bumper 38 is preferably constructed of a compliant material that may keep pressure against the electro-mechanical assembly 12 in the mounted configuration to limit or prevent vibration between the adsorbent containers 20 and the electro-mechanical assembly 12 in the mounted configuration. The airflow fitting 40 also preferably extends from the joining face 22 to provide flow channels between the compressor 14, the adsorbent containers 20 and a concentrated oxygen supply line (not shown) that provides concentrated oxygen to the patient. The bumper 38 may extend through a bumper hole 38a in the housing of the electro-mechanical assembly 12 at the second face 12b, may rest against the second face 12b or may be otherwise designed and configured to limit vibrations between the adsorbent containers 20 and the electro-mechanical assembly 12 in the mounted configuration. The bumper 38 is also not limited to being positioned on the joining face 22 of the adsorbent containers 20 and may be connected or secured to the clasp 30a, the airflow fitting 40, the second face 12b or on other components of the electro-mechanical assembly 12 or the adsorbent containers 20 to limit vibration and movement between the adsorbent containers 20 and the electro-mechanical assembly 12 in the mounted configuration. The configurable oxygen concentrator 10 may also include additional features for vibration limitation and control, such as active vibration controls, spring/damper mechanisms or other features that limit vibration between the electro-mechanical assembly 12 and the adsorbent containers 20 and the batteries 18. The vibration limitation features may be the same or similar for the batteries 18, as is described above with respect to the adsorbent containers 20, including bumpers 38, spring damper mechanisms or other vibration limiting features.

In use, the adsorbent containers 20 are preferably attached to the electro-mechanical assembly 12 by aligning the clasp 30a with the locking hole 30c, as well as the airflow fittings 40 and the bumpers 38 with their associated connecting slots/fittings/holes on the second face 12b of the electro-mechanical assembly 12. The adsorbent containers 20 are urged toward the second face 12b such that the ramped surface 30d contacts a lower edge of the locking hole 30c, thereby urging the clasp 30a and the translatable rod 30b upwardly relative to the adsorbent containers 20 or toward the upper shelf 32a against the bias of the spring 34. The adsorbent containers 20 are urged toward the second face 12b until a nose 30e of the ramped surface 30d passes the lower edge of the locking hole 30c such that the spring 34 urges the translatable rod 30b and the clasp 30a downwardly toward the lower shelf 32b so that the nose 30e engages an inside surface of the housing of the electro-mechanical assembly adjacent the locking hole 30c. The engagement of the nose 30e with the housing of the electro-mechanical assembly 12 secures the adsorbent containers 20 to the electro-mechanical assembly 12 in the mounted configuration. The positioning of the translatable rod 30b within the housing of the adsorbent containers 20 and the general inaccessibility of the clasp 30a in the mounted configuration generally prevents inadvertent release of the adsorbent containers 20 from the electro-mechanical assembly 12. It is desirable to maintain the attachment of the adsorbent containers 20 with the electro-mechanical assembly 12 once the adsorbent containers 20 are initially connected to the electro-mechanical assembly 12 to prevent exposure of the adsorbent materials to moisture in the air that will flow into the adsorbent containers 20 through the airflow fittings 50 once the adsorbent containers 20 are removes from the electro-mechanical assembly 12.

Figure 4:
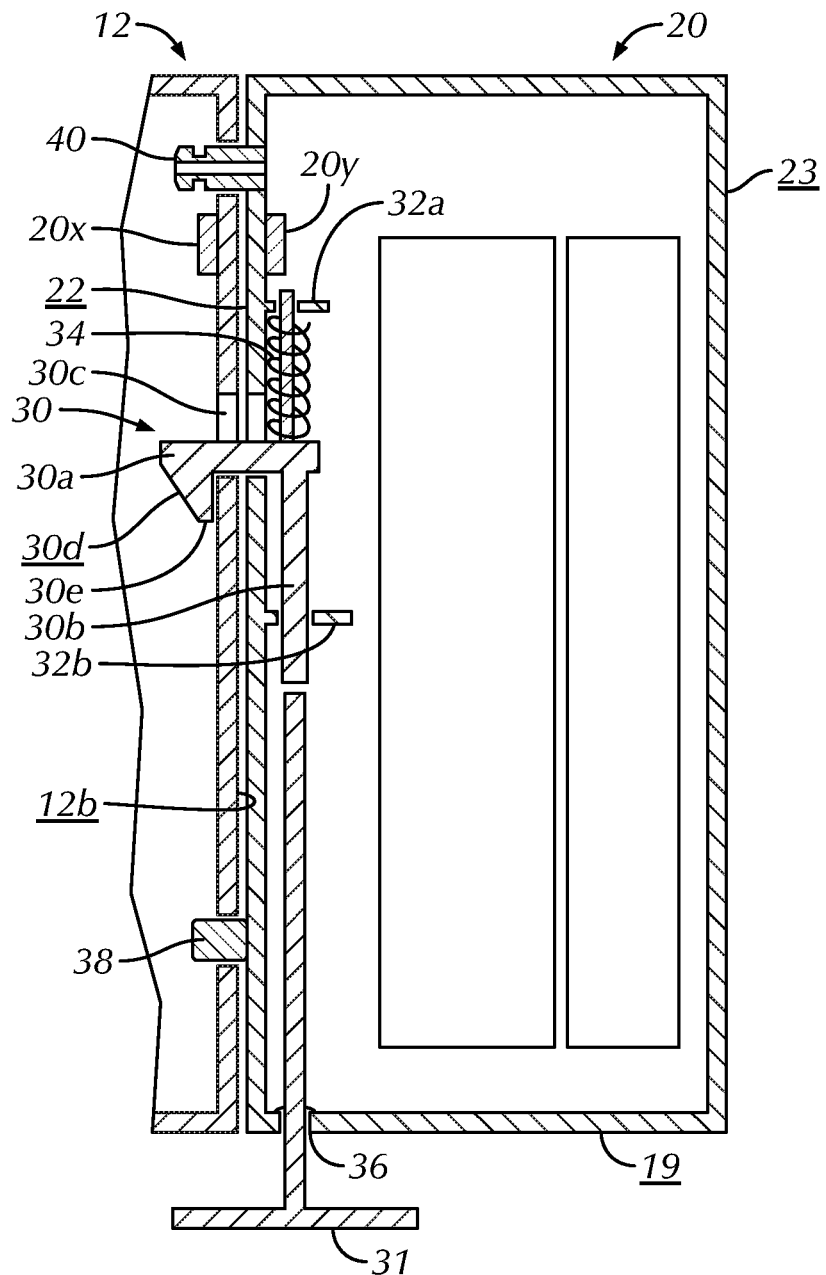
FIG. 4 is a cross-sectional view of an adsorbent container of the configurable oxygen concentrator of FIG. 1.

When a user desires, a physician requires or it is recommended based on use that the adsorbent container 20 connected to the electro-mechanical assembly 12 should be removed and replaced, a kit comprised of a replacement adsorbent container 20 and the release tool 31 may be sent to the user. The release tool 31 is inserted into the adsorbent container 20 through the release hole 36, as is shown in FIG. 4. The user urges the release tool 31 against a lower end of the translatable rod 30b and against the spring 34 to move the clasp 30a upwardly relative to the housing of the adsorbent container 20 and the housing of the electro-mechanical assembly 12. The rod 30b and clasp 30a are urged upwardly until the nose 30e clears the bottom edge of the locking hole 30c and the adsorbent container 30 may be pulled away from the electro-mechanical assembly 12 to release the adsorbent container 20 from the mounted configuration. The replacement adsorbent container 20 is then attached to the electro-mechanical assembly 12, as is described above and the release tool 31 may be disposed. The configurable oxygen concentrator 10 is not limited to the specifically described locking mechanism 30 and its related components and may include an alternative locking and release mechanism that is preferably difficult for the user to release inadvertently during use. Alternatively, the adsorbent module or container 20 may be provided with a retractable pull tab for removal of the adsorbent container 20 from the electro-mechanical assembly 12. The adsorbent container 20 is preferably removed by pulling on the tab or handle to slide the adsorbent container 20 out of the concentrator 10. A detent preferably holds the adsorbent container 20 in place within the concentrator 10.

Figure 5A:
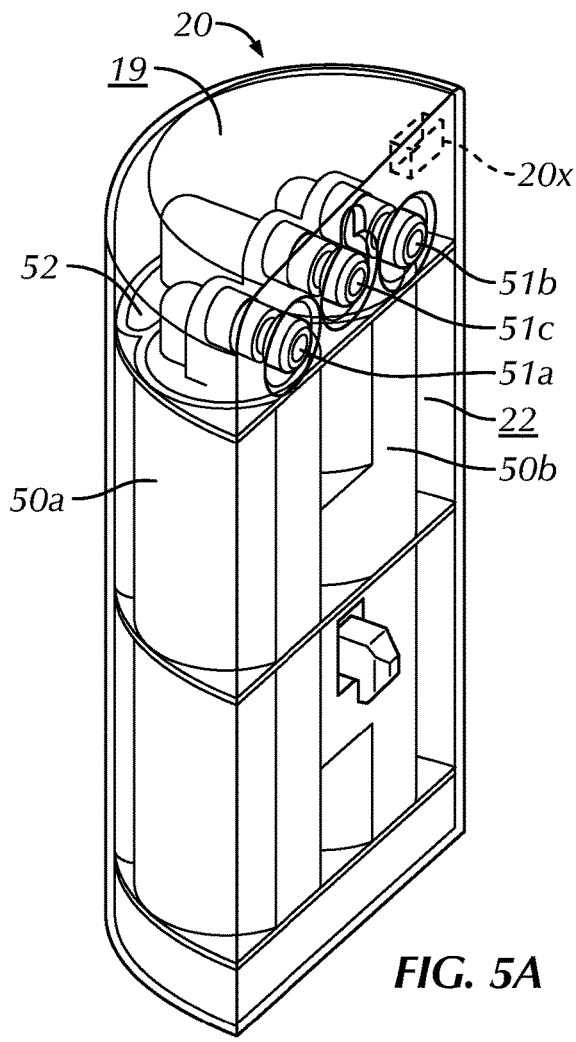
FIG. 5A is a side perspective, partially transparent view of an adsorbent container of the configurable oxygen concentrator of FIG. 1.
Figure 5B:
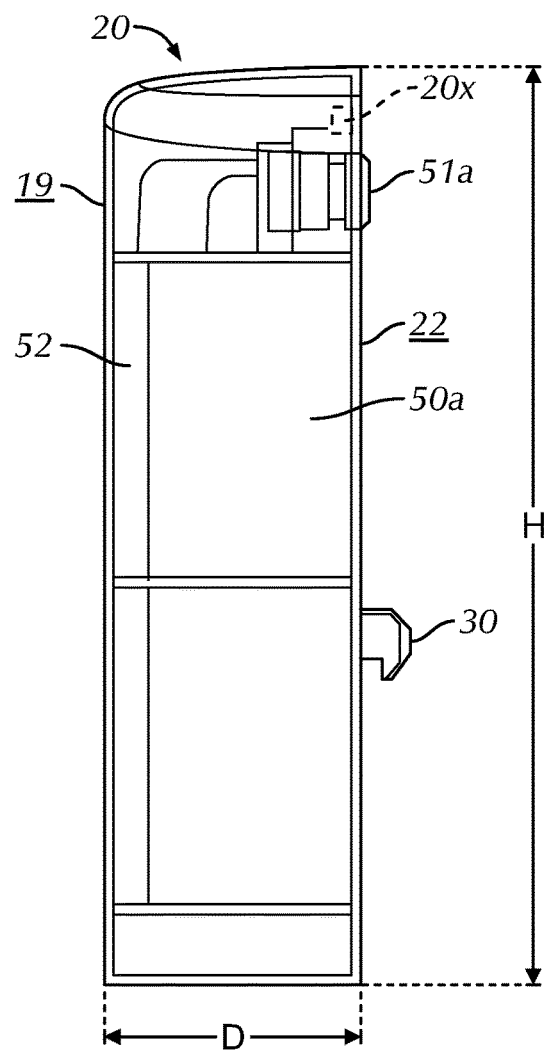
FIG. 5B is a side elevational, partially transparent view of the adsorbent container of FIG. 5A; 16b'
Figure 5C:
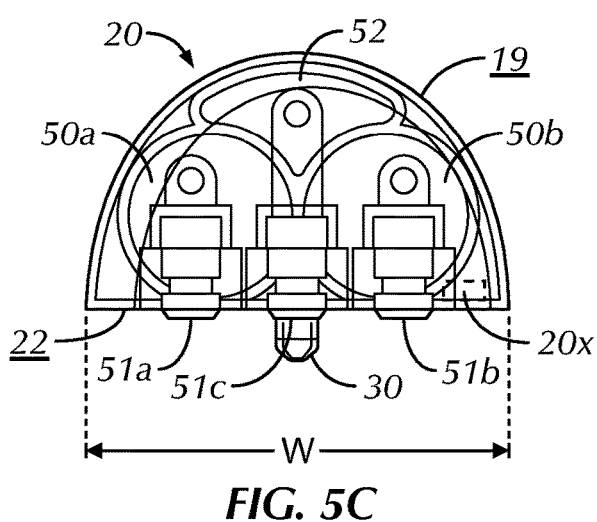
FIG. 5C is a top plan, partially transparent view of the adsorbent container of FIG. 5A.
Figure 6A:
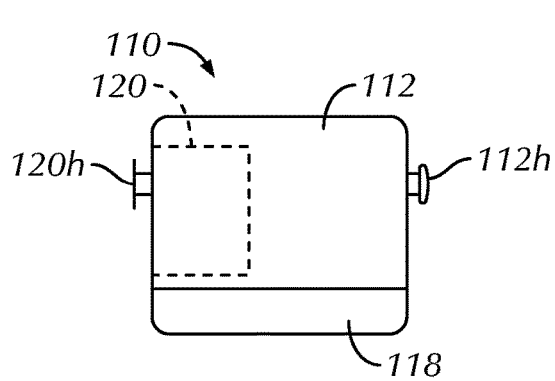
FIG. 6A is a front elevational sketch of a configurable oxygen concentrator in accordance with a second preferred embodiment of the present invention.
Figure 6B:
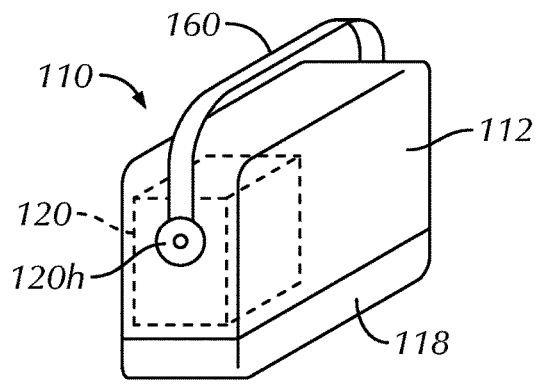
FIG. 6B is a front perspective sketch of the configurable oxygen concentrator of FIG. 6A with a carrying handle or strap.
Figure 6C:
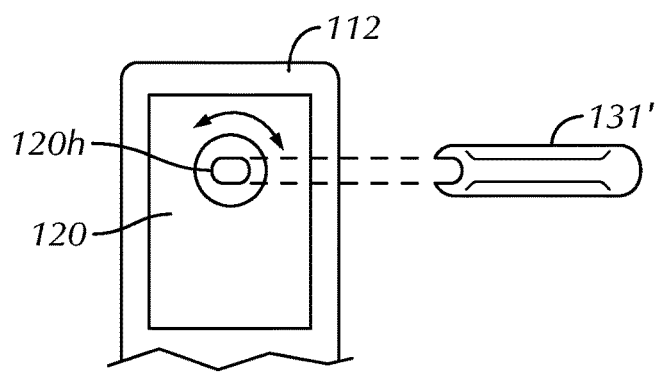
FIG. 6C is a side elevational sketch of the configurable oxygen concentrator of FIG. 6A, showing a side of an adsorbent container with a handle button and a release tool that may be utilized with the handle button to releasably secure the adsorbent container to an electro-mechanical assembly.
Figure 6D:
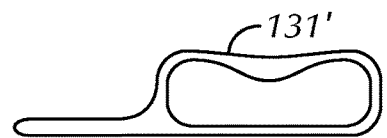
FIG. 6D is a side elevational view of the release tool of FIG. 6C for use with the configurable oxygen concentrator of FIG. 6A.
Figure 6E:
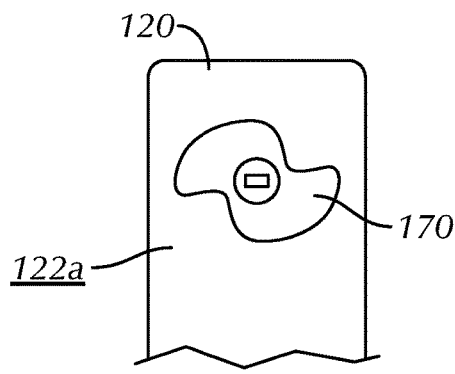
FIG. 6E is side elevational and partially cut-away view of the adsorbent container of the configurable oxygen concentrator of FIG. 6A, showing a locking mechanism in a locked configuration.
Figure 6F:
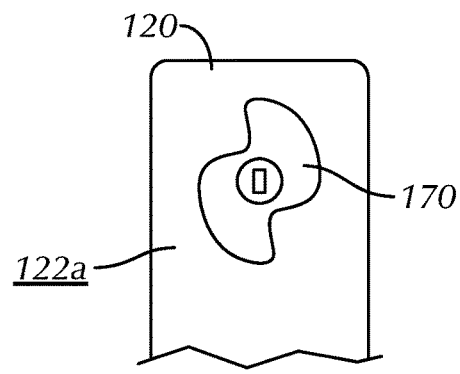
FIG. 6F is a side elevational and partially cut-away view of the adsorbent container of the configurable oxygen concentrator of FIG. 6A, showing the locking mechanism in an unlocked configuration

Referring to FIGS. 3-5, the adsorbent containers 20 include first and second adsorbent beds 50a, 50b with adsorbent material therein to facilitate separation of oxygen from the air and an oxygen reservoir 52 that stores the purified oxygen prior to directing the concentrated oxygen to the patient through the oxygen hose 26. The first and second adsorbent beds 50a, 50b and the oxygen reservoir 52 are preferably co-molded or integrally formed of a polymeric material. In the first preferred embodiment, the polymeric material is comprised of polyvinyledene chloride ("PVDC") or Polyvinylidene fluoride ("PVDF") and may be either filled or unfilled with a typical filler material, such as glass fiber. The preferred PVDC and PVDF materials are not limiting and the first and second adsorbent beds 50a, 50b may be constructed of alternative materials, but the PVDC and PVDF materials are preferred for their strength, structural integrity, low volatile organic compound ("VOC") emission, low permeability to moisture, and manufacturability. The co-molded adsorbent beds 50 and oxygen reservoir 52 may alternatively be constructed of another polymeric material that provides sufficient strength and stiffness to perform the preferred functions of the co-molded adsorbent beds 50 and oxygen reservoir 52, is able to withstand the normal operating conditions of the co-molded adsorbent beds 50 and oxygen reservoir 52, is generally able to retain the pressurized oxygen and air therein and otherwise is able to perform the preferred functions of the co-molded adsorbent beds 50 and oxygen reservoir 52. The preferred first, second and third adsorbent containers 20a, 20b, 20c have a height H, width W and depth D that is consistent across each size of the adsorbent containers 20. The size of the individual co-molded adsorbent beds 50 and oxygen reservoir 52 may change internally in the different adsorbent containers 20a, 20b, 20c, but the overall footprint is preferably maintained such that the overall footprint of the assembled configurable oxygen concentrator 10 generally does not change, regardless of which adsorbent container 20a, 20b, 20c is attached to the electro-mechanical assembly 12. The consistent footprint of the adsorbent containers 20a, 20b, 20c is not limiting and each of the adsorbent containers 20a, 20b, 20c may have different sizes, as is shown in FIG. 3. Placing both the adsorbent beds 50 and the oxygen reservoir 52 in the single adsorbent container 20 allows all pneumatic connections to be located at the same end of the adsorbent container 20, thus simplifying both the adsorbent containers 20 and a mating manifold design of the electro-mechanical unit 12. In the first preferred embodiment, the first adsorbent bed 50a is in fluid communication with a first connection fitting 51a, the second adsorbent bed 50b is in fluid communication with a second connection fitting 51b and the oxygen reservoir 52 is in fluid communication with a third connection fitting 51c extending from the joining face 22 of the adsorbent containers 20. The first, second and third connection fittings 51a, 51b, 51c mate with counterpart fittings (not shown) of the electro-mechanical assembly 12 for oxygen purification, storage and oxygen and air communication with the electro-mechanical assembly 12.

In addition, the inclusion of the co-molded oxygen reservoir 52 with the adsorbent beds 50a, 50b in the adsorbent containers 20 is preferred such that the oxygen reservoir 52 is not required in the electro-mechanical assembly 12. Typical oxygen concentrators include their oxygen reservoir within the electro-mechanical assembly or the main housing not in the replaceable adsorbent containers 20. The oxygen reservoirs of the typical oxygen concentrators are generally constructed of aluminum pressure vessels mounted in the main housing and require transport of oxygen through tubing communication with the sieve beds. The typical oxygen reservoirs, therefore, take up significant space in the housing or electro-mechanical unit and requiring sealing and oxygen transport across the attachment boundary to any replaceable sieve bed.

Referring to FIGS. 6A-6E, a second preferred embodiment of the configurable oxygen concentrator 110 for providing various flow rates and volumes of concentrated oxygen to a patient has a similar construction to the first preferred configurable oxygen concentrator 10 and like reference numbers are utilized to identify like features of the second preferred configurable oxygen concentrator with a number "1" prefix to distinguish the features of the configurable oxygen concentrator 10 of the first preferred embodiment from the configurable oxygen concentrator 110 of the second preferred embodiment.

The second preferred configurable oxygen concentrator 110 includes the electro-mechanical assembly 112 adapted for engagement with differently sized adsorbent containers 120 at a side of the electro-mechanical assembly 112 and with differently sized batteries 118 along a bottom of the electro-mechanical assembly 112. The electro-mechanical assembly 112 preferably includes a handle button 112h extending from a side surface opposite the second face 112b where the adsorbent containers 120 are connected and the adsorbent containers 120 preferably include a handle button 120h on a side opposite a joining face 122. The handle buttons 112h, 120h are releasably securable to a handle 160 for carrying the alternative preferred configurable oxygen concentrator 110. The handle button 120h on the adsorbent container 120 can also be utilized to pull or urge the adsorbent container 120 off of the electro-mechanical assembly 112.

The electro-mechanical assembly 112 of the second preferred embodiment may also be configured to include a space configured like a hole for a vertical drawer into which the adsorbent containers 120 are removably mounted to the electro-mechanical assembly 112. The handle button 120h, which is preferably shaped like a mushroom with a flat head and a slender stalk, includes flat spots on the stem. The second preferred embodiment also includes a release tool 131 that is releasably engageable onto the flats of the stem, like a wrench on a bolt, and under the head. To remove the adsorbent container 120 from the electro-mechanical assembly 112, the patient preferably slips the release tool 131 onto the flats with the release tool 131 oriented at a right angle to the vertical axis of the configurable oxygen concentrator 110. The patient would then turn the tool ninety degrees (90°) which also turns an oval shaped plate or other engagement mechanism 170 located under the surface or housing of the adsorbent bed 120. This plate or locking mechanism 170 locks the adsorbent container 120 to the electro-mechanical unit 112 by having the extreme axis of the oval engage with a groove in the housing of the electro-mechanical unit 112. The oval of the locking mechanism 170 would be preferably unlocked when the release tool 131 is vertical and locked when the release tool 131 is horizontal relative to the electro-mechanical unit 112 in a preferred orientation with the battery 118 positioned on the bottom of the unit. When unlocked the release tool 131 also preferably provides a finger hold so the patient can pull on the adsorbent container 120 to remove it or push on it to replace it, onto or off of the electro-mechanical unit 112. After replacement of the adsorbent container 120, the patient preferably turns the release tool 131 to a horizontal position and then slides the release tool 131 off of the handle button 120h. Alternatively, the adsorbent container 120 is provided with a foldable pull tab similar to those used in a beverage container and a détente preferably holds the adsorbent container 120 in place in a mounted configuration.

EXAMPLE CONFIGURATION 1

The first preferred configurable oxygen concentrator 10 has the electro-mechanical assembly 12 containing the compressor 14, valves and an associated manifold, electronic circuit boards, a cooling fan, and the user interface 16, including the display 16a, the selector dial 16b that permits selection of different concentrated oxygen flowrate within the specification of the concentrator 10 and the power button 16c. The electro-mechanical assembly 12 is preferably unchanged regardless of which of the batteries 18 or sieve modules 20 is attached to the electro-mechanical assembly 12. The electro-mechanical assembly 12 is roughly rectangular in cross-section and preferably has the interface 16, such as user controls and indicators on a top surface. The sieve or adsorbent modules 20 and batteries 18 are releasably connected to the opposite sides or first and second faces 12a, 12b of the electro-mechanical assembly 12. The batteries 18 preferentially house four (4), eight (8), twelve (12) or sixteen (16) individual rechargeable battery cells. The cells are connected to produce twelve volts (12 V) direct current. The sieve or adsorbent modules 20 preferentially contain two sieve beds and an oxygen reservoir. The individual sieve beds or adsorbent modules 20 preferentially contain thirty (30), forty (40), or fifty (50) grams of adsorbent material therein. A patient, who is in the early stages of COPD, may be prescribed oxygen at an equivalent flow rate of one or two liters per minute (1-2 LPM). A DME is selected to provide equipment to the patient for oxygen therapy. The DME selects the smallest adsorbent module 20a and connects it to the electro-mechanical assembly 12. Then the small and medium size batteries 18a, 18b are selected for use with the electro-mechanical assembly 12. The small battery 18a may be comprised of a fifty watt (50 W) hour battery that provides two and on-half to three and one-half hours (2½-3½ hrs) of oxygen for close to home activities. The preferred configurable oxygen concentrator 10, in this configuration, has the lightest components and is relatively easy for the patient to carry. The medium battery 18b may be configured to provide five to seven hours (5-7 hrs) of oxygen and can be used while the first or small battery 18a is charging. The entire configurable oxygen concentrator 10, in this configuration, preferably weights approximately two and one-half pounds (2½ lbs) making adherence to LTOT/Walk therapy relatively easy and simple for the patient due to the relatively light weight of the configurable oxygen concentrator 10. The first, small or low flow rate sieve or adsorbent module 20a is preferably operable at three settings that may be controlled from the selector dial 16b. The selector dial 16b is able to control the flow of concentrated oxygen to the patient, wherein the third setting is preferably able to provide more concentrated oxygen flow than is required by the patient's prescription for periods of increased exertion.

EXAMPLE CONFIGURATION 2

The patient described in example 1 has now progressed to the second stage of the breathing disease and their physician recommends an increased oxygen flow of three liters per minute (3 LPM) equivalent. The physician may write a prescription for this increased flow and the DME would have supplied a completely different concentrator to the patient in the prior art method, because the patient's relatively low flow concentrator would not be capable of providing this increased flow and the DME would have to receive and replace the old concentrator with a generally larger capacity concentrator that is able to provide the increased flow rate. This procedure entailed retrieving the original concentrator provided to the patient and then delivering the new concentrator with new operating instructions and training, if necessary. This is a time-consuming and expensive procedure for the DME and the patient and requires the patient to wait for the increased flow rate concentrator while the DME processes the new higher flow prescription. It also requires, in many cases, that the patient must purchase a new machine, which can be cost prohibitive for the patient and/or payor.

The design of the first preferred configurable oxygen concentrator 10, instead, allows the DME to supply only a different user replaceable next size larger sieve module 20b, 20c. In this case, the DME may provide the second or medium adsorbent module 20b or forty gram (40 g) per sieve bed module 20b. After receiving the prescription, the DME preferably sends the new higher volume flow rate second module 20b to the patient and the patient installs it after removing the first or smaller sieve module 20a. The new second module 20b sends a signal via an electrical communication connection, such as a magnetic proximity switch (not shown), to the electro-mechanical assembly 12 and the electronic controller in the electro-mechanical assembly 12 allows the new flow settings that are appropriate for the second adsorbent module 20b. The controller of the electro-mechanical assembly 12 makes any necessary adjustments to driving speed of the compressor 14 and delivery valve settings. The patient and DME are subjected to minimal expense and disruption of service, such as delays while the entire concentrator is returned and replaced, as is required with prior art concentrators. At the same time the DME may offer a battery upgrade to accommodate the increased electrical demand of the configurable oxygen concentrator 10 of the first preferred embodiment that may be required to drive the compressor 14 for operation with the larger second adsorbent module 20b. In addition, the DME may elect to supply an upgraded battery 18 with technology that was unavailable when the configurable oxygen concentrator 10 was introduced or first sold, resulting from improvements in battery technology subsequently developed.

EXAMPLE CONFIGURATION 3

The patient described in examples 1 and 2 has now progressed to the next stage of the breathing disease and requires the maximum flow that can normally be provided by a portable oxygen concentrator. This flow is typically, but not limited to, about four to five liters per minute (4-5 LPM) equivalent. So now an oxygen concentrator that can produce about one thousand milliliters per minute (1000 ml/m) is prescribed and a new concentrator must be supplied after the physician provides a prescription when the patient was confronted with this situation when using the prior art systems. The design of the preferred configurable oxygen concentrator 10 provides the third, larger flow rate sieve module or adsorbent container 22c that can accommodate this flow rate and is connectable to the electro-mechanical assembly 12. Again, the DME preferably sends the new sieve module, such as the third adsorbent container 20c, to the patient and the patient installs the third adsorbent module 20c just as they would a new battery 18, but the third adsorbent container 20c is attached to the second face 12b of the electro-mechanical assembly 12. The configurable oxygen concentrator 10 is now capable of producing the new flow rate and the electronic communication mechanism, such as the proximity switch, preferably senses the third sieve module 20c so that the controller makes any changes necessary for operation at the new flow settings. The third, larger battery 18c may be used to accommodate the increased electrical demand of the electro-mechanical assembly 12 when operated with the third adsorbent module 20c, but is not so limited and the configurable oxygen concentrator 10 may be operated with any of the preferred batteries 18 in combination with any of the adsorbent containers 20. The larger flow rate capacity of the third adsorbent container 20*c* may be due to its size, type of sieve material, layering of different sieve materials or combinations of these modifications to facilitate the larger flow rate capacity of the third adsorbent container 20*c*.

The first preferred configurable oxygen concentrator 10 may be configured having the smallest size and least weight for each stage of the patient's disease or may be adaptively configured such that the user, patient or medical professional is able to control weight, size and volumetric concentrated oxygen flow based on numerous factors associated with the patient and their treatment. The cost to reconfigure the configurable oxygen concentrator 10 is kept to a minimum, because only the sieve module or adsorbent container 20 may be upgraded as the preferred oxygen concentrator shifts from various volumetric flows, operational durations and related parameters. The sieve module 20 typically comprises approximately five percent (5%) of the cost of the entire concentrator 10. The alternative is for the DME to provide several prior art oxygen concentrators of varying sizes during the treatment regime of the patient, or to offer just one overly large concentrator that meets all flow requirements. This, however, makes compliance to the LTOT/walk therapy difficult.

The first preferred configurable oxygen concentrator 10 also preferably incorporates active and passive noise cancellation to limit the amount of sound or noise that the concentrator 10 generates during use. The active and passive noise cancellation is preferably adapted to limit noise generated in the various operating configurations and speeds contemplated for the concentrator 10. In the first preferred embodiment, the concentrator may include a microphone or transducer (not shown) positioned proximate the compressor 14 or other components that may generate noise that picks up the noise signals inside or proximate the concentrator 10. The microphone, transducer or other sound data collection instrument preferably collects noise or sound levels and other related information and transmits the data to the controller, which filters the collected data for major sound levels. The controller also preferably inverts the signal, sends the inverted signal to a speaker or transducer (not shown) inside the concentrator 10, thereby partially negating the original noise signal and making the external noise signal of a lower intensity. The microphone or transducer may be located on the interior or exterior surface of the concentrator 10 or nearly anywhere proximate the concentrator 10 for collection of sound and noise data. The controller may operate such that the inverted signal is subtracted from the original inverter signal, thereby preventing feedback. The user interface 16 may include a noise cancellation control selector (not shown) that permits activation or deactivation of the active noise cancellation system by the user, thereby giving the choice between lower energy use and quieter operation. The collected noise data from the microphone may be processed and inverted by the microphone, the controller or an electronic processor designed for active noise cancellation. The controller may also amplify the inverted signal to more nearly or closely equate the inverted signal to the intensity of the original noise signal. The controller may further be configured such that the inverted signal is selected to negate those frequencies which are most objectionable to persons in proximity to the concentrator 10.

Referring to FIGS. 7-16, a third preferred embodiment of a configurable oxygen concentrator 310 for providing various flowrates and volumes of concentrated oxygen has a similar construction to the first and second preferred configurable oxygen concentrators 10, 110 and like reference numbers are utilized to identify like features of the third preferred configurable oxygen concentrator with a number "3" prefix to distinguish the features of the configurable oxygen concentrator 310 of the third preferred embodiment from the configurable oxygen concentrators 10, 110 of the first and second preferred embodiments. The third preferred configurable oxygen concentrator 310 is also a modular oxygen concentrator 310, however, because the sieve module or adsorbent container 20 is contained within a housing 311 of the electro-mechanical assembly 312, the overall outer dimension of the configurable oxygen concentrator 310 does not substantially change when the different sieve modules or adsorbent containers 320 are inserted into the housing 311. The third preferred configurable oxygen concentrator 310 preferably includes multiple adsorbent containers 320 having different capacities, similar to the first, second and third adsorbent containers 20*a*, 20*b*, 20*c* of the first preferred embodiment, however, as each of the adsorbent containers 320 of the third preferred embodiment has substantially the same external dimensions, only a single adsorbent container 320 is shown in the drawings. The third preferred configurable oxygen concentrator 310 does, however, having multiple adsorbent containers 320 with different capacities that are preferably identifiable by the notification devices 320*x* of the adsorbent containers 320, which is sensed by the notification sensor 320*y* that in turn communicates the sensed information to the controller 317 in the working configuration.

Figure 7:
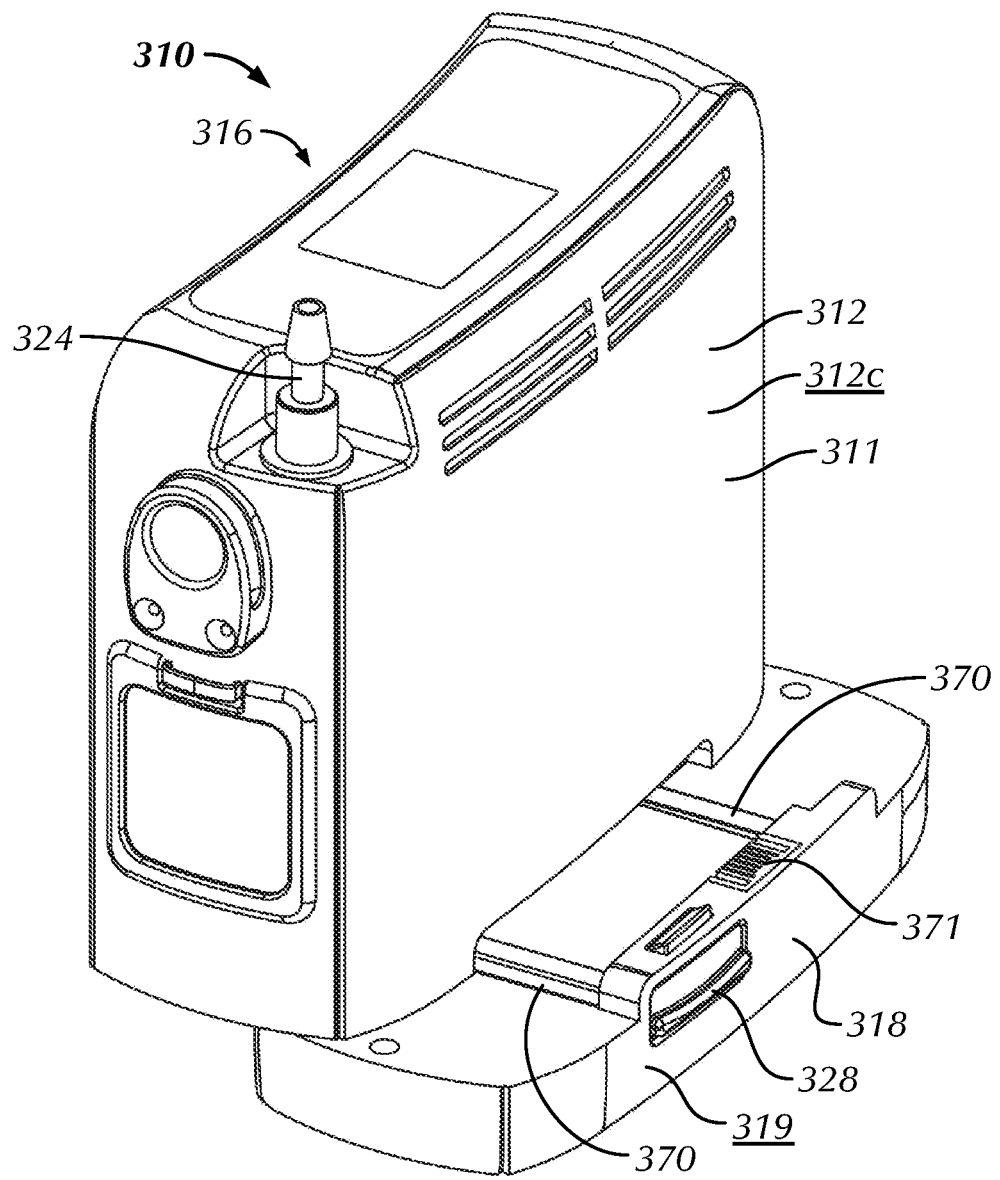
FIG. 7 is a top perspective, partially exploded view of a configurable oxygen concentrator in accordance with a third preferred embodiment of the present invention.
Figure 8:
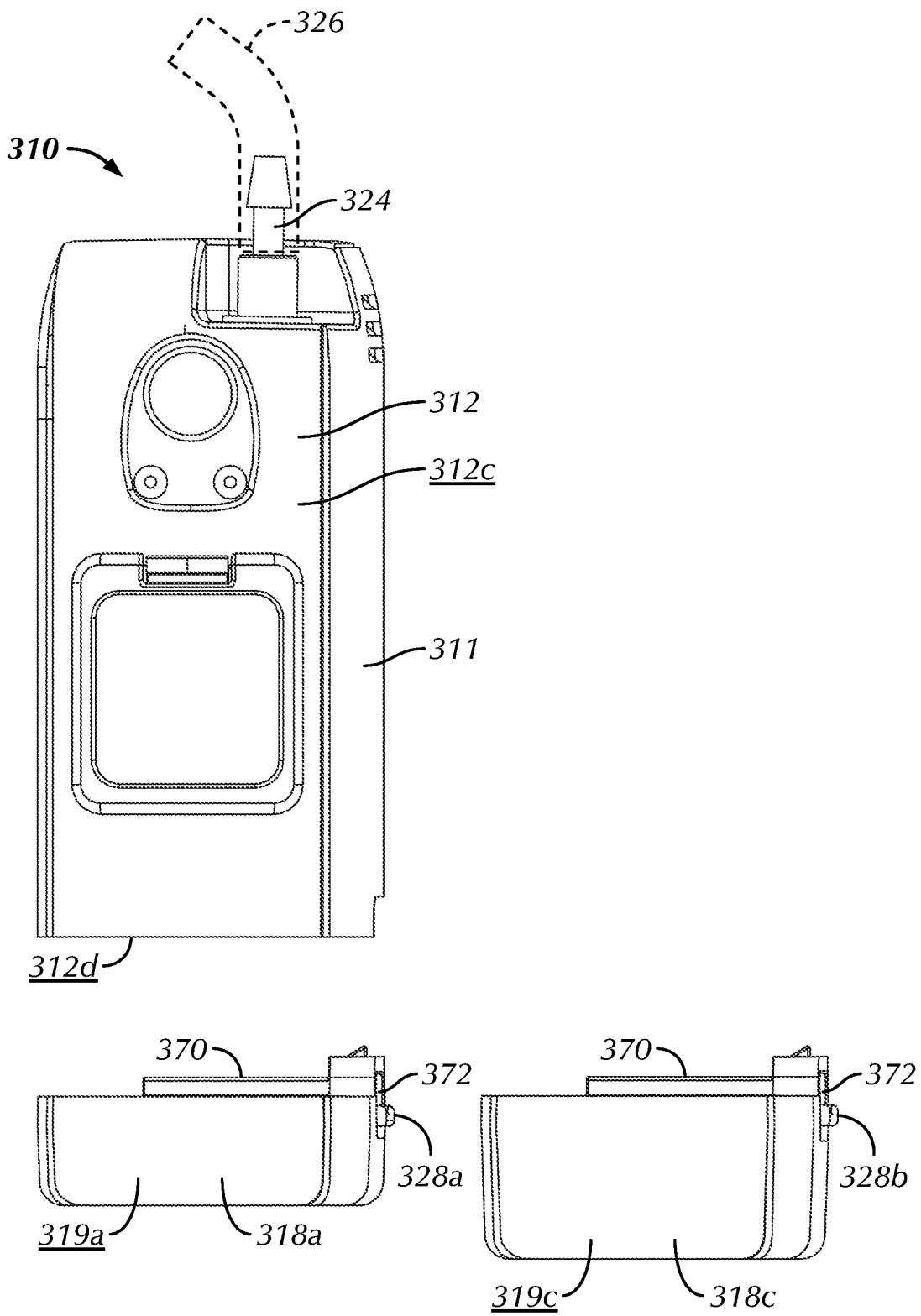
FIG. 8 is a side elevational, partially exploded view of the configurable oxygen concentrator of FIG. 7, wherein two differently sized batteries shown.
Figure 9:
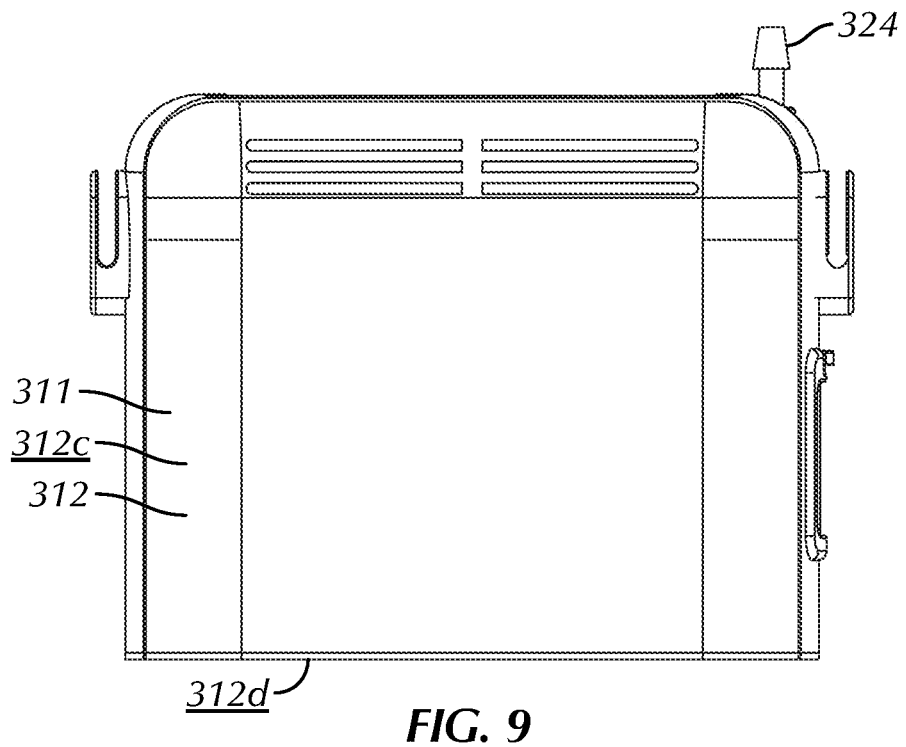
FIG. 9 is a rear elevational view of an electro-mechanical assembly of the configurable oxygen concentrator of FIG. 7.
Figure 10:
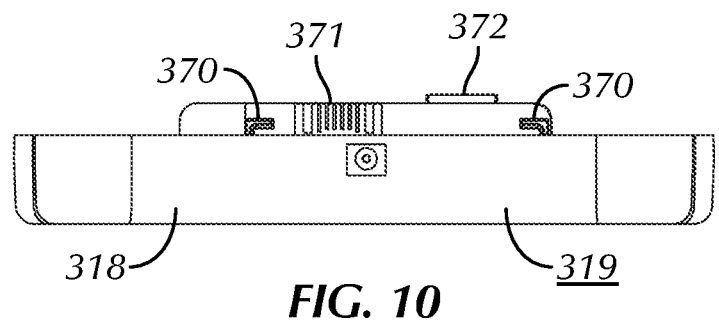
FIG. 10 is a rear elevational view of a battery of the configurable oxygen concentrator of FIG. 7.
Figure 11:
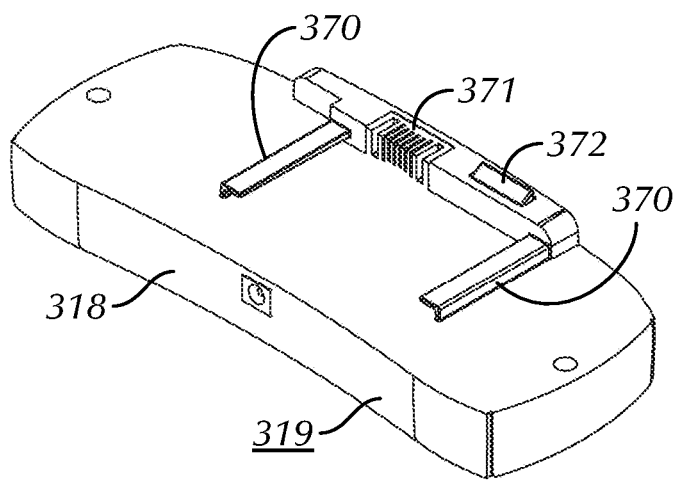
FIG. 11 is a top perspective view of the battery of FIG. 10.
Figure 14:
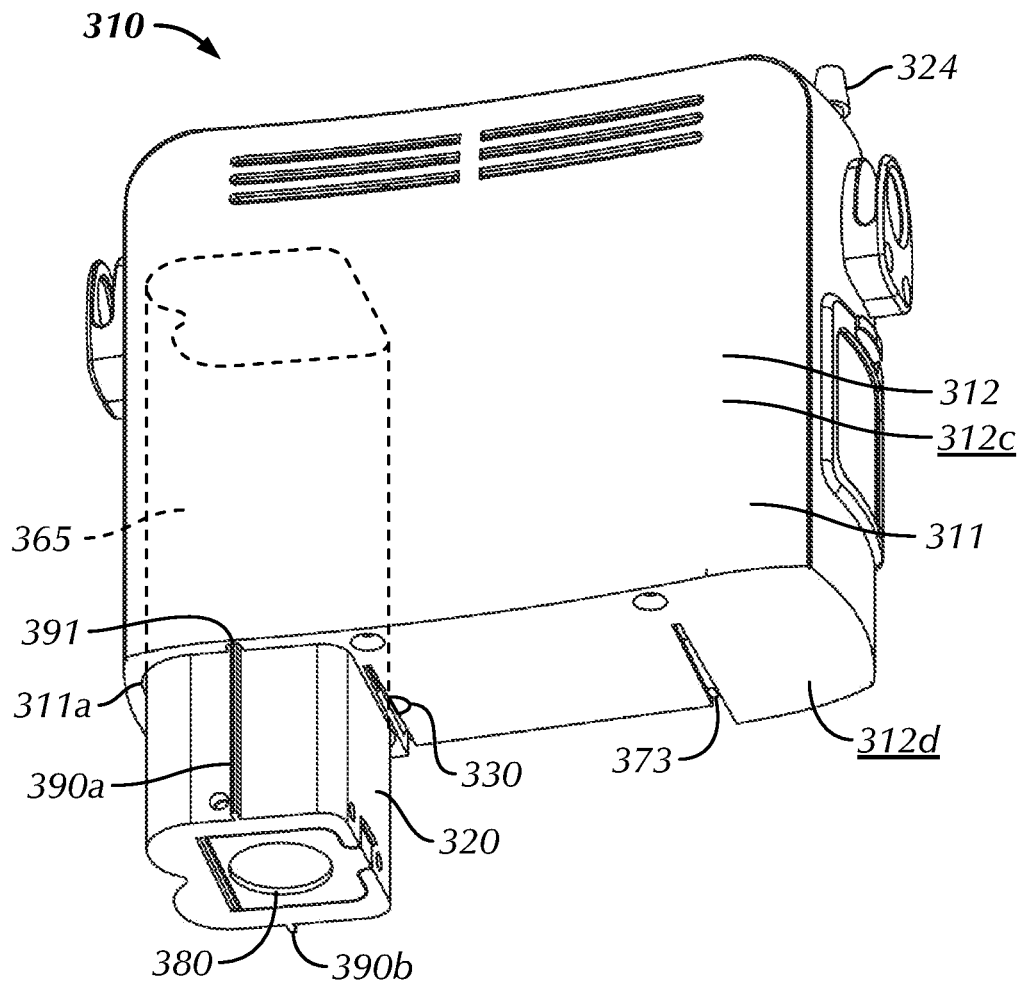
FIG. 14 is a bottom perspective, partially exploded view of the electro-mechanical assembly and adsorbent container of FIG. 12.

The third preferred oxygen concentrator 310 preferably has a slight end-to-end curve from a left-side to a right-side, as is shown in at least FIG. 7. The slight curve of the oxygen concentrator 310 in the working configuration permits a user to rest the concave front of the concentrator 310 against their body during transport and facilitates positioning or nesting of the concentrator 310 against the user's body during use. The concentrator 310 may, for example, be carried with a carrying strap that positions the concentrator 310 against the side of the user's body with the concave front side proximate the user's side.

In the third preferred embodiment the different sieve modules or adsorbent containers 320 are inserted through a bottom of the housing 311 of the electro-mechanical assembly 312, but other versions could include sieve modules or adsorbent containers 320 inserted from the back, top, front or side of the housing 311. The bottom insertion of the sieve modules or adsorbent containers 320 into the housing 311 permits locking of the sieve modules or adsorbent containers 320 within the housing 311 by mounting one of the batteries 318 over a sieve insertion hole 311*a* in the housing 311. The third preferred batteries 318 are external, replaceable, rechargeable batteries 318, such as, for example fifty watt-hour (50 Whr), one hundred watt-hour (100 Whr), one hundred fifty watt-hour (150 Whr) or other sized and designed batteries 318. The batteries 318 are preferably slidably mountable onto the electro-mechanical assembly 312 at the base of the electro-mechanical assembly 312, such that their weight is evenly distributed at the base of the configurable oxygen concentrator 310. The batteries 318 preferably slide onto the bottom of the electro-mechanical assembly 312, completing the outside form of the configurable oxygen concentrator 310 in an assembled configuration. In the working configuration (FIG. 12), similar to the first preferred embodiment, the outer surface 319 of the batteries 318 define a substantially continuous, uninterrupted surface with the outer surface 312*c* of the housing of the electro-mechanical assembly 312. The batteries 318 also preferably cover the insertion hole 311a, which blocks removal of the adsorbent containers 320 while the batteries 318 are mounted to the electro-mechanical assembly 312. To remove/replace the adsorbent containers 320, the batteries 318 are removed from the electro-mechanical assembly 312.

The various adsorbent containers 320, having different capacities, having substantially the same outer dimensions for insertion into the sieve insertion hole 311a. The batteries 318 are mountable over the sieve insertion hole 311a in the working configuration to block the adsorbent containers 320 in the housing of the electro-mechanical assembly 312. The various capacity adsorbent containers 320 are mounted in a container cavity 365 in the working configuration within the housing 311. The configurable oxygen concentrator 310 of the third preferred embodiment includes at least first and second adsorbent containers 320 having different capacities and may have three or more adsorbent containers 320, each having different capacities, similar to the first, second and third adsorbent containers 20a, 20b, 20c of the first preferred embodiment, except the adsorbent containers 320 of the third preferred embodiment have substantially the same outer dimensions for insertion into the container cavity 365 in the working configuration. The notification sensor 320y detects the notification device 320x when one of the adsorbent containers 320 is mounted in the container cavity 365 and transmits a signal to the controller 317 so that the controller 317 operates the electro-mechanical assembly 312 in accordance with which adsorbent container 320 is mounted in the container cavity 365. The controller 317 preferably operates the electro-mechanical assembly 312 to produce different volumes of purified oxygen for the user based on which adsorbent container 320 is mounted to the electro-mechanical assembly 312 or provides options or settings for production of different levels of purified oxygen delivery to the user based on the adsorbent container 320 mounted to the electro-mechanical assembly 312. The controller 317 may alternatively automatically direct the electro-mechanical assembly 312 to deliver a predetermined volume of purified oxygen to the user based on which adsorbent container 320 is attached to the electro-mechanical assembly 312, such as four hundred milliliters per minute (400 ml/min) for a first smaller capacity adsorbent container 320 and eight hundred milliliters per minute (800 ml/min) for a second larger capacity adsorbent container 320.

The third preferred adsorbent containers 320 also include the first and second adsorbent beds 350a, 350b with adsorbent or zeolite material therein to facilitate separation of oxygen from the air and the oxygen reservoir 352 that stores the purified oxygen prior to directing the concentrated oxygen to the patient through the oxygen hose 26. The first and second adsorbent beds 350a, 350b and the oxygen reservoir 352 are preferably co-molded or integrally formed of a polymeric material, preferably PVDC or PVDF and may be either filled or unfilled with a typical filler material, such as glass fiber. The co-molded adsorbent beds 350 and oxygen reservoir 352 may alternatively be constructed of another polymeric material that provides sufficient strength and stiffness to perform the preferred functions of the co-molded adsorbent beds 350 and oxygen reservoir 352, is able to withstand the normal operating conditions of the co-molded adsorbent beds 350a, 350b and oxygen reservoir 352, is generally able to retain the pressurized oxygen and air therein and otherwise is able to perform the preferred functions of the co-molded adsorbent beds 350, 350b and oxygen reservoir 352. The preferred adsorbent containers 320 of the third preferred embodiment have substantially the same outer dimensions to fit into the container cavity 365.

The size of the individual co-molded adsorbent beds 350a, 350b and oxygen reservoir 352 may change internally in the different adsorbent containers 320, but the overall footprint is preferably maintained such that the overall footprint of the electro-mechanical assembly 312 in the working configuration generally does not change, regardless of which adsorbent container 320 is attached to the electro-mechanical assembly 12. The consistent footprint of the adsorbent containers 320 is not limiting and each of the adsorbent containers 320 may have different sizes, in accordance with the first preferred embodiment. Placing both the adsorbent beds 350a and the oxygen reservoir 352 in the electro-mechanical unit 312 allows all pneumatic connections to be located at the same end of the adsorbent container 320, thus simplifying both the adsorbent containers 320 and a mating manifold design of the electro-mechanical unit 312. The first adsorbent bed 350a is in fluid communication with a first connection fitting 351a, the second adsorbent bed 350b is in fluid communication with a second connection fitting 351b and the oxygen reservoir 352 is in fluid communication with a third connection fitting 351c extending from the a top surface of the adsorbent containers 20. The first, second and third connection fittings 351a, 351b, 351c mate with counterpart fittings (not shown) of the electro-mechanical assembly 312 for oxygen purification, storage and oxygen and air communication with the electro-mechanical assembly 312. The top mounted first, second and third connection fittings 351a, 351b, 351c facilitate mating of the fittings 351a, 351b, 351c with counterpart fittings (not shown) of the electro-mechanical assembly 312 wherein the adsorbent containers 320 are slidable into the container cavity 365 from the bottom of the housing 311.

The batteries 318 of the third preferred embodiment include two L-shaped rails 370 that slide into L-shaped grooves 373 in the bottom of the electro-mechanical assembly 312. The L-shaped grooves 373 extend inwardly from one side of the housing 311 of the electro-mechanical assembly 312 and terminate before an opposing end of the housing 311. The L-shaped rails 370 extend from an electrical connector 371 on the batteries 318 at one end of the batteries 318 and terminate before reaching an opposing end of the batteries 318. The L-shaped rails 370 and the L-shaped grooves 373 facilitate sliding attachment of the batteries 318 to the housing 311 and the electrical connector 371 connects to a mating connector (not shown) on the housing 311 to electrically connect the batteries 318 to the electro-mechanical assembly 312. The batteries 318 also include a lock mechanism 372 that releasably locks the batteries 318 into place to the housing 311 in a mounted configuration (FIG. 12) and releases the batteries 318 from the housing 311 when actuated by the user. The batteries 318 and housing 311 are not limited to including the specifically shown and described L-shaped grooves 373, L-shaped rails 370 and the lock mechanism 372 and may be otherwise configured to removably mount the batteries 318 to the housing 311.

The electro-mechanical assembly 312 includes the outer surface 312c that creates a substantially continuous surface with the outer surfaces 319, 319a, 319c of the batteries 319 in the working configuration. In the third preferred embodiment, specifically, the side, front and back outer surfaces 312c of the housing 311 create a substantially continuous surface with the side, front and back outer surfaces 319, 319a, 319b of the batteries 319 in the working configuration. The housing 311 of the third preferred embodiment includes a bottom surface 312d and the batteries 318, 318a, 318c are removably mountable over the bottom surface 312d.

In the third preferred embodiment, a base or beginning model of the configurable oxygen concentrator or portable oxygen concentrator ("POC") 310 may include a four (4) cell battery or first battery 318a and a first sieve module or first adsorbent container 320a with enough zeolite or adsorbent material to produce what is commonly referred to as a three liter (3 L) pulse dose equivalent flow of oxygen or alternatively equivalent to six hundred milliliter per minute (600 ml/min) of oxygen. The third preferred configurable oxygen concentrator 310 is capable of operating at three levels, for example, corresponding to one liter (1 L), two liter (2 L) and three liter (3 L) pulse dose equivalent flow of oxygen.

As a patient's COPD progresses, i.e. deteriorating lung capacity, and they require oxygen to be delivered at an equivalent four liter (4 L) or five liter (5 L) level, an alternative sieve module or adsorbent bed 320, capable of delivering oxygen at all five levels could be inserted into the housing 311 in exchange for the lower performing three liter (3 L) sieve module or adsorbent bed 320. The patient may also elect to increase the size of the battery 318 to an eight (8) cell battery in order to maintain the higher oxygen concentration level requirements of the modified POC 310. In the third preferred embodiment, the configurable oxygen concentrator 310 is designed for use with the three liter (3 L) equivalent and below adsorbent container 320 and the five liter (5 L) equivalent and below adsorbent container 320 that are substantially the same size and fit into the sieve insertion hole 311a of the housing 311 for use with the electro-mechanical assembly 312.

A notification device 320x of the adsorbent container 320 signals, electronically, optically, mechanically or otherwise, to the controller the configuration of the adsorbent container 320 and the controller operates the electro-mechanical assembly in accordance with predetermined programs based on the size and configuration of the mounted adsorbent container 320. The notification device 320x preferably communicates with a notification sensor 320y mounted in the electro-mechanical assembly 312. The notification sensor 320y is, in turn, in communication with the controller 317. The notification device 320x may be a magnet that signals the controller by the Hall effect to modify operation and enable the appropriate oxygen flow. The third preferred configurable oxygen concentrator 310 is not limited to the two described adsorbent containers 320 with the three liter (3 L) and below operating capacity and the five liter (5 L) and below operating capacity and may be otherwise designed and configured for operation at different levels that are also preferably identified by interaction between the notification device 320 on the adsorbent container 320 and the controller of the electro-mechanical assembly 312.

In the third preferred embodiment, the differently configured adsorbent beds or containers 320 have substantially the same outer dimensions for insertion into the sieve insertion hole 311a and mounting within the housing 311, but include features that facilitate different performance of the adsorbent beds 320. The different adsorbent beds 320 may have different sizes and configurations of zeolite or sieve material therein, may be operated at faster cycle times to quickly fill the oxygen reservoir or may be otherwise designed and configured to provide differing levels of capacity during operation of the configurable oxygen concentrator 310. The adsorbent containers 320 also preferably include opposing guide rails 390a, 390b that ride in opposing guide grooves 391 in the housing 311 to guide the adsorbent beds or containers 320 into and out of the housing 311 and the container cavity 365. The configurable oxygen concentrator 310 is not limited to including the opposing guide rails 390a, 390b and the opposing guide grooves in the housing 311 and may include any alternative mechanism to guide the adsorbent containers 320 into and out of the housing 311 or may not include any guiding mechanisms, without significantly impacting the operation of the configurable oxygen concentrator 310. Placing both the adsorbent container 320 and the oxygen reservoir in the electro-mechanical unit 312 allows all pneumatic connections to be located at the same end of the adsorbent container 320, thus simplifying both the adsorbent containers 320 and a mating manifold design of the electro-mechanical unit 312.

An advantage of the modular and configurable oxygen concentrator 310 is to allow a patient to minimize the weight of the POC or concentrator 310 at the early stages of the disease by using the lighter sieve module or adsorbent container 320 and the lighter battery 318. As the disease progresses and more oxygen is needed or a different purity of oxygen is required, the patient can simply modulate/upgrade the size or functions of the sieve module or adsorbent container 320 and battery performance without having to change or buy an entire new POC 310 or, particularly, replace the electro-mechanical assembly 312. Known oxygen concentrators may sell for over two thousand US dollars ($2,000) a piece. Utilizing the modular and configurable oxygen concentrator 310 of the third preferred embodiment facilitates the ability of the patient to eliminate the need to spend several thousand dollars on two oxygen concentrators if, for example, they happened to initially purchase a POC that only performs at, for example, a two or three liter (2 or 3 L) equivalent level, but subsequently require performance at a greater than three liter (3L) level as their disease progresses.

The sieve modules or adsorbent containers 320 of the third preferred embodiment have the same or substantially the same outside dimensions, regardless of the volume of zeolite or active material contained therein and regardless of the level at which the adsorbent containers 320 are designed to operate. This allows the electro-mechanical assembly 312 and related hardware, such as a carrying case (not shown) to be manufactured with a single size receiving configuration for the sieve module or adsorbent container 320, thereby reducing the cost of manufacturing the third preferred configurable oxygen concentrator 310.

The adsorbent containers 320 of the third preferred embodiment are removably insertable into the housing 311 through the sieve insertion hole 311a. The housing 311 preferably has a release button or cam/spring mechanism or détente 330 that automatically snaps over the bottom of the adsorbent containers 320 when the adsorbent container is positioned in a working position within the housing 311. The cam/spring mechanism 330 may be pivotable or slidable into and out of the sliding path of the adsorbent container 320 when being inserted into or removed from the housing 311. The cam/spring mechanism 330 preferably is releasable for removal and replacement of the adsorbent containers 320, as is described herein. When the cam/spring mechanism 330 snaps over the bottom of the adsorbent container 320 in the working position, the batteries 318 may be mounted over the bottom end of the housing 311 to further secure the adsorbent containers 320 in the housing 311. The adsorbent containers 320 may also include a handle or pull tab 380 on their bottom to assist in removing the adsorbent containers 320 from the housing 311 out of the working position.

Each sieve module or adsorbent container 320 in this third preferred embodiment includes a magnet, RFID chip or other sensor/notification device 320x that may be read to inform the controller 317 of the electro-mechanical assembly 312 that either a three liter (3 L), a five liter (5 L) or another sized sieve module or adsorbent container 320 has been inserted into housing 311 through the sieve insertion hole 311a. Based on the identification of the size and design function of the adsorbent container 320 mounted in the housing 311, the controller is able to modify the function and operation of the compressor 314 and related valves of the third preferred configurable oxygen concentrator 310 to provide the desired level of oxygen to the patient through the oxygen output fitting 324 and the oxygen hose 326. The same identification and operational modification would apply to the configurable oxygen concentrator 310 that has a different size and function when compared to the configurable oxygen concentrator 310 shown in FIGS. 7-14, such as a configurable oxygen concentrator used for a wound care application. Variously designed adsorbent containers 320 that are designed to perform at different oxygen concentration and flow levels and to fit into the housing 311 through the sieve insertion hole 311a are preferably interchangeable with the configurable oxygen concentrator 310 for various patients, diseases, functions and operations.

Modularity provides additional benefits, such as the ability to accommodate supplemental oxygen supply for recreational or non-medical purposes and in industrial applications, such as high altitudes where the percentage of oxygen in air drops below the sea level standard of approximately nineteen to twenty percent (19-20%) oxygen, seventy-nine percent (79%) Nitrogen and one percent (1%) Argon and other gases. Patients or users with normal lung function generally do not need ninety-five percent (95%) pure oxygen at high altitude, but could utilize oxygen-enriched air that is, for example, bursts or bolus' of fifty to sixty percent (50-60%) oxygen during exertion or at intervals to oxygenate their blood supply. When using the preferred configurable oxygen concentrator 310, the sieve module or adsorbent container 320 can be designed to produce only fifty to sixty percent (50-60%) oxygen to reduce such problems as light headedness or altitude sickness. The magnet, other sensor or notification device 320x may be configured to transmit an instruction to the processor or controller of the electro-mechanical assembly 312 in the POC or concentrator 310 that instructs and drives the controller to operate the compressor 314 and other components of the concentrator 310 such that only the reduced level of oxygen purity is produced at the oxygen output fitting 324 for the patient. The identification of this desired, lower operating oxygen purity for the configurable oxygen concentrator 310 is desirable so that the preferred concentrator 310 avoids alarms and warnings that are often when oxygen purity output at the output fitting 324 drops below approximately eighty-two to eighty-five percent (82-85%). The alarms and warnings are typical for medical oxygen concentrators when minimum acceptable oxygen purity for a medically prescribed POC is sensed. Sieve modules or adsorbent containers 320 with different amounts and sizes of zeolites could be built to perform a range of different oxygen purities and flows and such configuration is available with the third preferred configurable oxygen concentrator 310.

Referring to FIGS. 12-16, another application of modular sieve beds, consumer replaceable sieve beds or adsorbent containers 320 and the configurable oxygen concentrator 310 is in the medication, drug and supplement delivery field. The material within the preferred adsorbent containers 320, an attachment in the airflow of the configurable oxygen concentrator 310, a drug eluting tube 360 attached to the adsorbent containers 320 or within an oxygen storage container 362 that is mounted within the electro-mechanical assembly 312 or other device may be attached within the airflow of the preferred configurable oxygen concentrator 310 to supply medication, drugs, supplements, aromatics or other materials to the patient. For example, in the wound care field, topical oxygen can increase or otherwise improve the healing process of a wound. Topical oxygen can be delivered via such mechanisms as a hyperbaric chamber or sealed bandage or sleeve via a cannula connected to the configurable oxygen concentrator 310. Antibiotics or other medications, drugs, supplements or other materials may be introduced into the concentrated oxygen flow, such as through the drug eluting tube 360 that emits drugs, such as antibiotics, into the purified oxygen flow for direct exposure to the wound. Alternatively, the drug eluting tube 360 may be impregnated or loaded with a narcotic, hemp oil, cannabidiol, antihistamine, steroid or other medication for introduction into the patient's lungs for direct absorption. The drug eluting tube 360 may be removable and replaceable and may be activated by heat or electrical stimulation such that the drug is only released into the purified oxygen stream when directed by the controller 17, through heating or electrical stimulation. Further, the medication may be associated with the replaceable adsorbent container 320, which may be removed and replaced after a predetermined amount of running time. The electro-mechanical assembly 312 may also include a sensor (not shown) in communication with the controller 317 that senses the level of medication within the purified oxygen stream and initiates a warning to the patient when the concentration level of the medication in the purified oxygen stream reaches a minimum level, indicating removal and replacement of the adsorbent container 320 for a new adsorbent container 320 with a fresh load of medication is desired. The electro-mechanical assembly 312 may also be configured to indicate or present a warning to the user after the preferred concentrator 310 runs for a predetermined amount of time or for a combination of an amount of time and at particular levels that indicate the incorporated medication is exhausted, thereby recommending replacement of the medication. The drug eluting tube 360 may also be mounted within the housing 311 of the electro-mechanical assembly 312 in fluid communication with the adsorbent containers 320 in the working configuration for introduction of medication or drugs into the enriched oxygen stream before the $O_2$ enriched air is directed to the patient through the oxygen output fitting 324. The drug eluting tube 360 and/or the oxygen storage container 362 may be considered a therapeutic eluting container for introducing therapeutics into the purified oxygen stream for the benefit of the patient.

The preferred electro-mechanical assembly 312 also includes a communication device, such as a wireless transponder or a storage mechanism that is able to save and transmit collected data to a central server. The communication device is able to download data, such as oxygen concentration, movement of the concentrator 310, time, level of operation of the concentrator 310, global positioning system ("GPS") location information of the concentrator 310, chemical sensors and related data that may be collected by the concentrator 310 and transmitted to a physician to assist in diagnosis or therapy for the patient. The patient may also utilize an app that communicates with the communication device to provide analysis and therapy suggestions to the patient or to provide reminders for therapy to the patient. The app may further provide warnings to the patient based on the collected data, such as suggestions to reorder new adsorbent containers 20, 120, 320, replace or order new batteries 18, 118, 318, low oxygen levels or other warning or suggestions.

In addition to delivering oxygen to a wound, medication, drugs or supplements could be added to the flow of topical oxygen to a wound with the configurable oxygen concentrator 310. Medicine or supplements could be added via a venturi apparatus containing the medication, drug or supplements. Alternatively, the medication, drug or a supplement could be added to the oxygen storage/reservoir column 362 of the electro-mechanical assembly 312 via the drug eluting tube 360, directly to the oxygen storage container 362, an attachment to the oxygen storage container 362 or other mechanisms. The medication could be introduced or injected via a one way valve on the oxygen storage/reservoir column 362 or via a resorbable or eluting coating inside the oxygen storage column 362. The third preferred configurable oxygen concentrator 310 may also be utilized for bi-level positive airway pressure ("BPAP") and continuous positive airway pressure ("CPAP") therapies, which may also incorporate delivery of medication and other materials to the patient. The configurable oxygen concentrator 310 of the third preferred embodiment may be operated in a similar or the same manner as oxygen delivery device or oxygen concentrator described in International Patent Application Publication No. WO 2017/165749, titled "Positive Airway Pressure System with Integrated Oxygen," and filed on Mar. 24, 2017, the contents of which are incorporated herein by reference in their entirety.

The third embodiment may include a removable screw cap 364 that has a post 366 or reservoir full of medication, drug or supplement for introduction into the purified oxygen. Such medication, drug or supplement on the post 366 could also be delivered from a manufacturer, preloaded in the sieve module or adsorbent container 320 or be introduced by a patient or medical professional at a later time by simply screwing in the medication, drug or supplement post 366 on the cap 364.

By way of example and by no means limiting the scope of the medical, industrial and recreation applications of the configurable oxygen concentrator 310, one example would be to introduce an antibiotic into the oxygen storage/reservoir container 362 where the POC or configurable oxygen concentrator 310 is being used for topical wound care/healing.

Alternatively, respiratory medications or supplements could be preloaded or later introduced by a patient or medical professional at a later time into the purified oxygen flow of the configurable oxygen concentrator 310.

Continued smoking by COPD patients on prescription oxygen commonly occurs. A nicotine eluting module for introduction into the purified oxygen flow could be created, potentially reducing cravings to smoke cigarettes for the patient.

Figure 15:
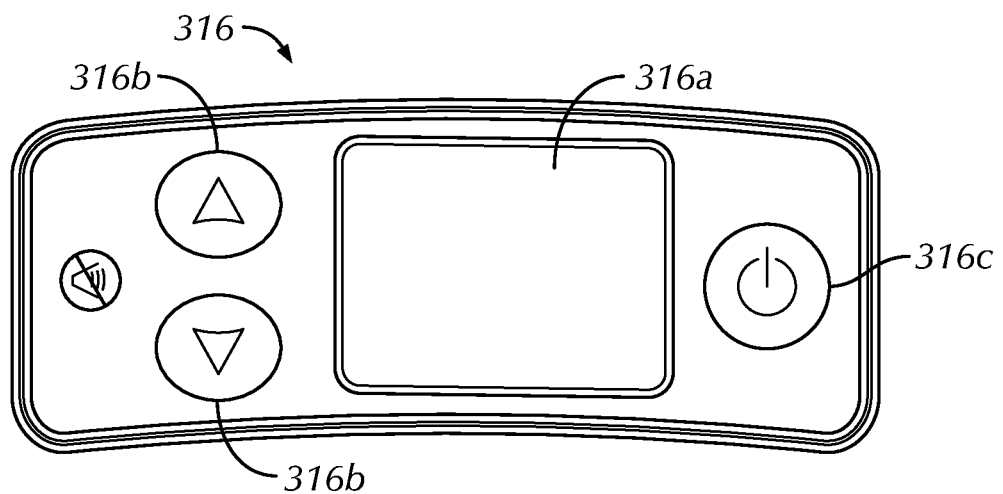
FIG. 15 a top plan view of a user interface of the configurable oxygen concentrator of FIG. 7.
Figure 16:
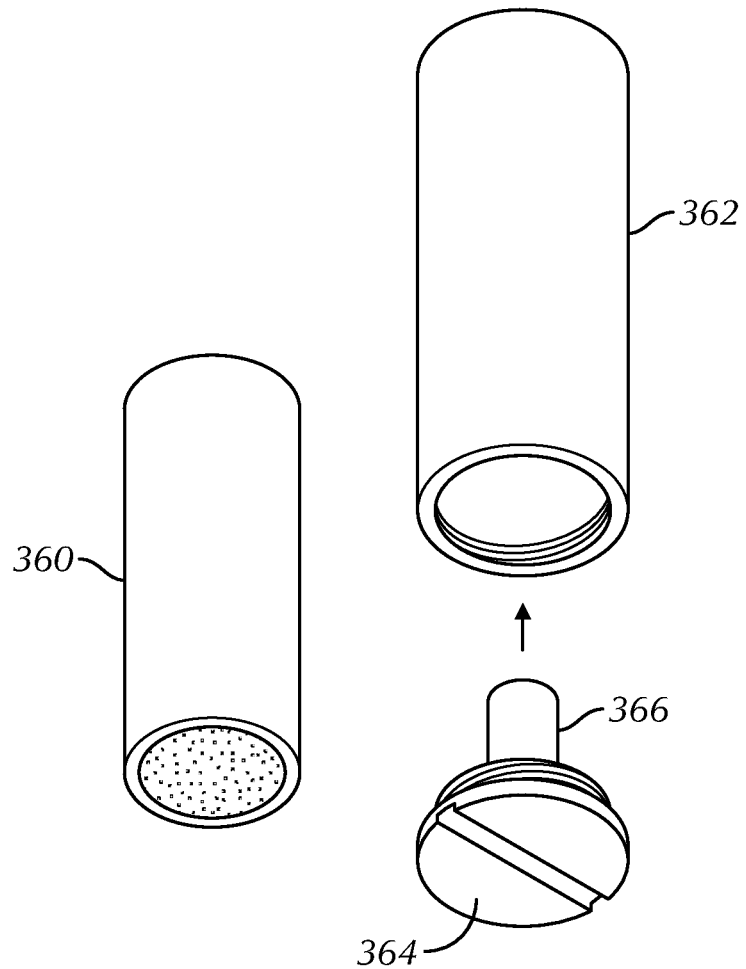
FIG. 16 is a side perspective, partially exploded view of a therapeutics eluting container of the configurable oxygen concentrator of FIG. 7.

Referring to FIG. 15, in the third preferred embodiment, the preferred portable oxygen concentrator 310 includes the user interface 316 that has similar features when compared to the first preferred user interface 16. The third preferred user interface 316 includes the display 316a the selector 316b, which is comprised of up and down buttons, that functions as the selector dial 16b and the power button 316c. The display 316a preferably shows five operating settings for the configurable oxygen concentrator 310, identified by the numbers "1," "2," "3," "4," and "5," which may represent the concentrator 310 working at five different operating levels, such as flow rates of approximately two hundred, four hundred, eight hundred and one thousand milliliters per minute (200, 400, 600, 800, 1000 ml/min). The flow rates and levels are not limiting, but are provided as non-limiting examples for the preferred portable configurable oxygen concentrator 310. The operating levels are preferable modified by manipulating the selector 316b to move the levels up and down, based on physician prescription, user preferences or other factors.

It is also considered with the third preferred embodiment that the controller 317 could be physically wired or wirelessly connected to a pulse oximeter (not shown) that transmits blood oxygen saturation levels to the controller 317 such that a warning is provided on the display 316a or otherwise informing the user their blood oxygen saturation level has dropped below or is exceeding a prescribed or preferred level. Alternatively, the controller 317 may automatically adjusts the oxygen flow level or oxygen purity to achieve the prescribed or desired blood oxygen saturation level. A normal healthy person should be able to achieve normal blood oxygen saturation levels or peripheral capillary oxygen saturation ("SpO2") of approximately ninety-four percent to ninety-nine percent (94-99%). For patients with mild respiratory diseases, the SpO2 should be approximately ninety percent (90%) or above. Supplementary oxygen should be used if SpO2 levels fall below ninety percent (90%), which is unacceptable for a prolonged period of time. Typically, patients monitor their SpO2 on a regular basis. Connecting a pulse oximeter to the controller 317 is beneficial to the user if and when the user is sleeping, unconscious or not otherwise able to sense or readily measure a material change in blood oxygen saturation levels It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present disclosure.

We claim:

1. A portable and configurable oxygen concentrator for providing various flow rates and volumes of concentrated oxygen to a patient, the oxygen concentrator comprising:
    an electro-mechanical assembly including a housing, the housing enclosing a compressor and valves, a user interface mounted to the housing, the compressor configured to produce pressure for the various flow rates and volumes of concentrated oxygen to the patient;
    a first battery having a first battery capacity, the first battery removably mountable to the electro-mechanical assembly;
    a first adsorbent container having a first adsorbent capacity, a first notification device associated with the first adsorbent container;
    a controller configured to direct the electro-mechanical assembly to produce an oxygen volume of purified oxygen; and
    a notification sensor mounted to the electro-mechanical assembly and in communication with the first notification device when the first adsorbent container is mounted to the electro-mechanical assembly, the notification sensor in communication with the controller, the controller configured to modify a function and operation of the compressor and the valves to provide a desired level of oxygen to the patient based on identification of the first notification device by the notification sensor.

2. The oxygen concentrator of claim 1, wherein the housing has an outer surface and the first battery has a first battery outer surface, the first battery outer surface forming a substantially continuous surface with the outer surface when the first battery is mounted to the housing.

3. The oxygen concentrator of claim 1, further comprising:
a second adsorbent container with a second notification device associated with the second adsorbent container, the second notification device in communication with the notification sensor when the second adsorbent container is mounted to the electro-mechanical assembly.

4. The oxygen concentrator of claim 3, wherein the notification sensor is configured to sense one of the first and second notification devices and provide a signal to the controller.

5. The oxygen concentrator to claim 1, wherein the notification sensor is comprised of a Hall effect sensor.

6. The oxygen concentrator of claim 1, wherein the notification sensor is comprised of a proximity sensor.

7. The oxygen concentrator of claim 1, wherein the notification sensor is comprised of an optical sensor, the first notification device is comprised of a first barcode.

8. The oxygen concentrator of claim 1, further comprising:
a second adsorbent container, the first adsorbent container includes a first volume of adsorbent material and the second adsorbent container includes a second volume of adsorbent material, the first volume being less than the second volume.

9. The oxygen concentrator of claim 1, wherein further comprising:
a second adsorbent container, the housing includes a sieve insertion hole, the first and second adsorbent containers having substantially the same outer dimensions for insertion into the sieve insertion hole.

10. The oxygen concentrator of claim 9, wherein the first battery is mountable over the sieve insertion hole in the working configuration.

11. The oxygen concentrator of claim 1, wherein the first adsorbent container is mountable in a container cavity within the housing in the working configuration.

12. The oxygen concentrator of claim 1, further comprising:
a drug eluting tube mounted within the electro-mechanical assembly, the drug eluting tube in flow communication with the first adsorbent container in the working configuration when the first adsorbent container is mounted to the electro-mechanical assembly.

13. The oxygen concentrator of claim 1, wherein the first battery has a first battery joining face and a first battery outer surface, the housing of the electro-mechanical assembly having a first face and an outer surface, the first battery removably mountable to the first face such that the first battery joining face is positioned proximate to the first face and the first battery outer surface and the outer surface form a substantially continuous surface in the working configuration.

14. The oxygen concentrator of claim 13, further comprising:
a second battery having a second battery joining face and a second battery outer surface, the second battery having a second battery capacity, the second battery capacity being greater than the first battery capacity, the second battery removably mountable to the first face such that the second battery joining face is positioned proximate the first face and the second battery outer surface and the outer surface form a substantially continuous surface in the working configuration.

15. The oxygen concentrator of claim 1, further comprising:
a second adsorbent container having a second adsorbent capacity; and
a third adsorbent container having a third adsorbent capacity, a third container outer surface and a third container joining face, the first adsorbent container having a first container joining face and a first container outer surface, the second adsorbent container having a second container joining face and a second container outer surface, the first, second and third adsorbent containers removably mountable to a second face of the housing such that the first, second or third container joining face is positioned proximate the second face and the first, second or third container outer surface and the outer surface of the housing forms a substantially continuous surface in the working configuration, the third adsorbent capacity being greater than the second adsorbent capacity.

16. The oxygen concentrator of claim 1, wherein the housing includes a sieve insertion hole with opposing guide grooves, the sieve insertion hole exposing a container cavity within the housing, the first adsorbent container including opposing guide rails, the opposing guide rails configured to ride in the opposing guide grooves to guide the first adsorbent container into the container cavity through the sieve insertion hole when inserting the first adsorbent container into the housing.

17. The oxygen concentrator of claim 1, wherein the first adsorbent container includes a first adsorbent bed, a second adsorbent bed and an oxygen reservoir.

18. The oxygen concentrator of claim 1, further comprising:
a second adsorbent container having a second adsorbent capacity, the controller operating such that the oxygen volume is a first oxygen volume of purified oxygen when the first adsorbent container is mounted to the electro-mechanical assembly and a second oxygen volume of purified oxygen when the second adsorbent container is mounted to the electro-mechanical assembly, the second oxygen volume being different than the first oxygen volume.

19. A portable and configurable oxygen concentrator for providing various flow rates and volumes of concentrated oxygen to a patient, the oxygen concentrator comprising:
an electro-mechanical assembly including a housing enclosing a compressor, the housing having a sieve insertion hole that exposes a container cavity within the housing;
a first adsorbent container having a first adsorbent capacity, the first adsorbent container removably mountable in the container cavity through the sieve insertion hole;
a first notification device associated with the first adsorbent container;
a second adsorbent container having a second adsorbent capacity, the second adsorbent container removably mountable in the container cavity through the sieve insertion hole, the second adsorbent capacity being greater than the first adsorbent capacity; a second notification device associated with the second adsorbent container; and
a notification sensor mounted to the electro-mechanical assembly and in communication with the first notification device when the first adsorbent container is mounted in the container cavity and in communication with the second notification device when the second adsorbent container is mounted in the container cavity in the working configuration, respectively, the controller operating such that the oxygen volume is a first oxygen volume of purified oxygen when the first adsorbent container is mounted in the container cavity and a second oxygen volume of purified oxygen when the second adsorbent container is mounted in the container cavity, the second oxygen volume being different than the first oxygen volume.

20. The oxygen concentrator of claim 19, wherein the second oxygen volume is greater than the first oxygen volume.

21. The oxygen concentrator of claim 19, wherein the first notification device is comprised of a first magnet, the second notification device is comprised of a second magnet and the notification sensor is comprised of a Hall-effect sensor.

* * * * *